(12) United States Patent
Pohlmann et al.

(10) Patent No.: US 8,486,413 B2
(45) Date of Patent: Jul. 16, 2013

(54) IMMUNOLOGICAL COMPOSITIONS AS CANCER THERAPEUTICS

(75) Inventors: Paula R. Pohlmann, Nashville, TN (US); Raymond L. Mernaugh, Franklin, TN (US); Carlos L. Arteaga, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 13/314,841

(22) Filed: Dec. 8, 2011

(65) Prior Publication Data

US 2012/0201820 A1 Aug. 9, 2012

Related U.S. Application Data

(60) Provisional application No. 61/421,052, filed on Dec. 8, 2010.

(51) Int. Cl.
*A61K 38/00* (2006.01)
(52) U.S. Cl.
USPC .......... 424/185.1; 424/138.1; 424/139.1; 424/155.1; 424/141.1
(58) Field of Classification Search
None
See application file for complete search history.

(56) References Cited

U.S. PATENT DOCUMENTS

2010/0215647 A1 8/2010 Pohlmann et al.

OTHER PUBLICATIONS

Baert et al., "Influence of immunogenicity on the long-term efficacy of infliximab in Crohn's disease," *NE J. Med.*, 348:601-608, 2003.
Bartelds et al., "Clinical response to adalimumab: relationship to anti-adalimumab antibodies and serum adalimumab concentrations in rheumatoid arthritis ," *Annals Rheumatic Dis.*, 66:921-926, 2007.
Ben-Kasus et al. "Persistent elimination of ErbB-2/HER2-overexpressing tumors using combinations of monoclonal antibodies: relevance of receptor endocytosis," *Proc. Natl. Acad. Sci.*, 106:3294-3299, 2009.
Disis et al., "Concurrent trastuzumab and HER2/neu-specific vaccination in patients with metastatic breast cancer ," *J. Clin. Oncol.*, 27:4685-4692, 2009.
Gjelstrup et al., "The role of higher-order protein structure in supporting binding by heteroclitic monoclonal antibodies: the monoclonal antibody KIM185 to CD18 also binds C4-binding protein," *Molecul. Immunol.*, 2011.

*Primary Examiner* — Sean E Aeder
*Assistant Examiner* — Julie Wu
(74) *Attorney, Agent, or Firm* — ParkerHighlander, PLLC

(57) ABSTRACT

The present invention concerns antibodies that react immunologically with an epitope comprising VDKSRWQQG (SEQ ID NO: 1), including those that bind to cancer cells, and methods relating thereto. In particular, the antibodies that react immunologically with a particular epitope found in anti-tumor antigen antibodies are not only indicative of favorable therapy using the anti-tumor antigen antibodies, but are therapeutic in and of themselves.

15 Claims, 9 Drawing Sheets

FIG. 3A-D

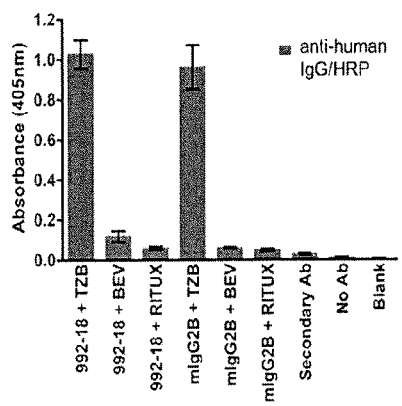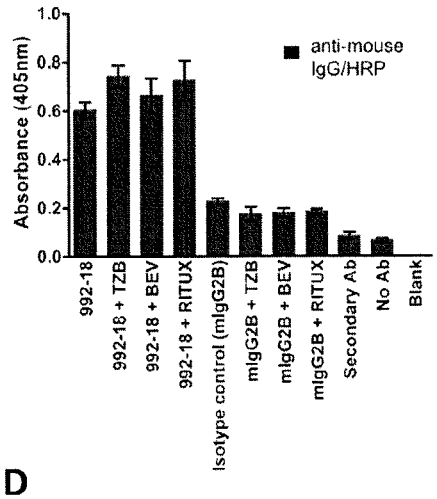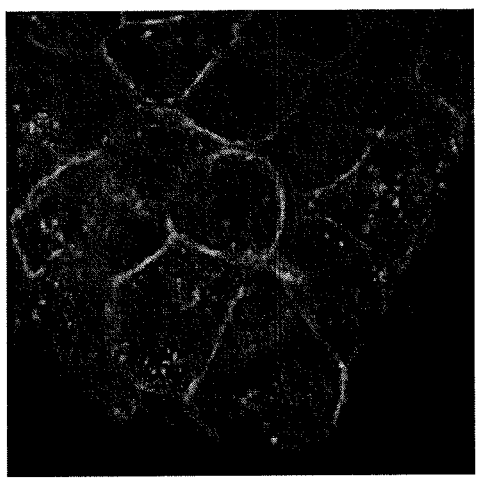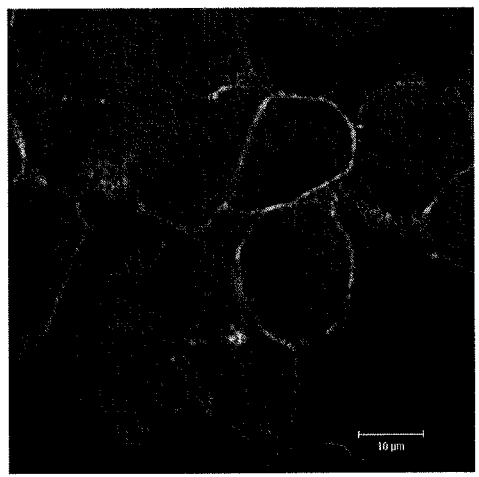
FIG. 5A-D

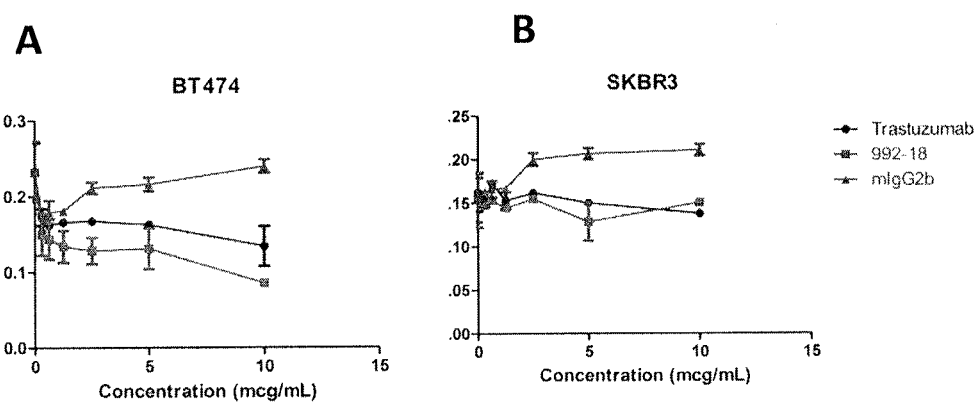
FIG. 6A-B

SEQUENCE LISTING

```
<160> NUMBER OF SEQ ID NOS: 3

<210> SEQ ID NO 1
<211> LENGTH: 9
<212> TYPE: PRT
<213> ORGANISM: Artificial Sequence
<220> FEATURE:
<223> OTHER INFORMATION: Synthetic peptide

<400> SEQUENCE: 1

Val Asp Lys Ser Arg Trp Gln Gln Gly
1               5

<210> SEQ ID NO 2
<211> LENGTH: 18
<212> TYPE: PRT
<213> ORGANISM: Artificial Sequence
<220> FEATURE:
<223> OTHER INFORMATION: Synthetic peptide

<400> SEQUENCE: 2

Val Asp Lys Ser Arg Trp Gln Gln Gly Asn Val Phe Ser Cys Ser Val
1               5                   10                  15

Met His

<210> SEQ ID NO 3
<211> LENGTH: 18
<212> TYPE: PRT
<213> ORGANISM: Artificial Sequence
<220> FEATURE:
<223> OTHER INFORMATION: Synthetic peptide

<400> SEQUENCE: 3

Ser Phe Phe Leu Tyr Ser Lys Leu Thr Val Asp Lys Ser Arg Trp Gln
1               5                   10                  15

Gln Gly
```

US 8,486,413 B2

IMMUNOLOGICAL COMPOSITIONS AS CANCER THERAPEUTICS

PRIORITY

This application claims benefit of priority to U.S. Provisional Application Ser. No. 61/421,052, filed Dec. 8, 2010, the entire contents of which are hereby incorporated by reference.

STATEMENT REGARDING FEDERALLY SPONSORED RESEARCH OR DEVELOPMENT

This invention was made with government support under Grant Nos. NCI R01 CA62212, R01 CA80195, P50 CA98131 and P30 CA68485 awarded by the National Institutes of Health. The government has certain rights in the invention.

FIELD OF THE INVENTION

The present invention concerns at least the fields of cell biology, molecular biology, and cancer therapy, diagnosis, and prognosis. In particular, the present invention relates to methods and compositions regarding antibodies that bind antibodies directed to a tumor antigen.

BACKGROUND OF THE INVENTION

Approximately 50% of patients with ERBB2 (which may also be referred to as HER2) positive breast cancer develop cellular and humoral immune response to ERBB2 (Disis et al., 1994). Antibodies are directed both to ectodomains and to intracellular domains of ERBB2. Furthermore, both IgG and IgM anti-ERBB2 has been detected. Higher titers of endogenous Ab anti-ERBB2 ECD are present in earlier breast cancer clinical stages (Disis et al., 1997). In fact, spontaneous immune responses to all members of the ERBB family (EGFR, ERBB2, ERBB3, ERBB4) have been detected (Bei et al., 1999). Also, little is known about the effects of the endogenous antibodies on phosphorylation of ERBB2 and its downstream signaling. T cell proliferation assays also show reactivity to ERBB2 epitopes, but the meaning of this response is unknown as well.

According to the immune network hypothesis, if there is an immune response with antibody (Ab1) production, there will be a regulatory response, with production of another antibody (Ab2) directed to Ab1. Little is known about the presence of endogenous Ab directed to anti-HER2 Abs in subjects, or their potential meaning or impact on disease or treatments.

Trastuzumab is a humanized monoclonal antibody (MAb) approved for treatment of HER2-overexpressing breast cancer. The inventors have previously detected trastuzumab-reactive (TR-)antibodies in the serum of patients treated with trastuzumab. These naturally occurring antibodies were associated with better treatment outcome in a preclinical model and in a small cohort of patients with HER2-overexpressing breast cancer and treated with trastuzumab. However, the potential for such antibodies to themselves be therapeutic has not been examined.

SUMMARY OF THE INVENTION

Thus, in accordance with the present invention, there is provided a monoclonal antibody that reacts immunologically with an epitope characterized by the primary sequence VDKSRWQQG (SEQ ID NO: 1). The monoclonal antibody may react immunologically with an epitope characterized by the primary sequence VDKSRWQQGNVFSCSVMH (SEQ ID NO:2) and/or SFFLYSKLTVDKSRWQQG (SEQ ID NO:3). The monoclonal antibody may further be defined as being produced by hybridoma cell line 992-18. The monoclonal antibody may be an IgG antibody. The monoclonal antibody may binds to a cancer cell, such as a breast cancer cell an ovarian cancer cell, a stomach cancer cell, a uterine cancer cell, a lung cancer cell, a prostate cancer cell, an esophageal cancer cell, a colorectal cancer cell, a head and neck cancer cell, a kidney cancer cell, a pancreatic cancer cell, a sarcoma cell, a melanoma cell, or a hematologic cancer cell (lymphomas/leukemias/myeloma). The monoclonal antibody may be a recombinant single-chain variable antibody fragment, a Fv fragment, a Fab antibody fragment or be humanized.

Also provided is a hybridoma that produces a monoclonal antibody that reacts immunologically with an epitope characterized by the primary sequence VDKSRWQQG (SEQ ID NO: 1). Thy hybridoma may further be defined as producing a monoclonal antibody may react immunologically with an epitope characterized by the primary sequence VDKSRWQQGNVFSCSVMH (SEQ ID NO:2) and/or SFFLYSKLTVDKSRWQQG (SEQ ID NO:3), or a monoclonal antibody that is an IgG antibody. The hybridoma may be designated as 992-18. The hybridoma may be further defined as producing a monoclonal antibody that binds to a breast cancer cell, an ovarian cancer cell, a stomach cancer cell, a uterine cancer cell, a lung cancer cell, a prostate cancer cell, an esophageal cancer cell, a colorectal cancer cell, a head and neck cancer cell, a kidney cancer cell, a pancreatic cancer cell, a sarcoma cell, a melanoma cell, or a hematologic cancer cell (lymphomas/leukemias/myeloma). The hybridoma may further be defined as producing a recombinant single-chain variable antibody fragment, a Fv fragment, or a humanized antibody.

Also provided is a composition comprising a monoclonal antibody that reacts immunologically with an epitope characterized by the primary sequence VDKSRWQQG (SEQ ID NO: 1) in a pharmaceutically acceptable buffer, carrier or diluent. The monoclonal antibody of the composition may react immunologically with an epitope characterized by the primary sequence VDKSRWQQGNVFSCSVMH (SEQ ID NO:2) and/or SFFLYSKLTVDKSRWQQG (SEQ ID NO:3). The monoclonal antibody of the composition may further be defined as being produced by hybridoma cell line 992-18. The monoclonal antibody of the composition may be an IgG antibody. The monoclonal antibody of the composition may binds to a cancer cell, such as a breast cancer cell, an ovarian cancer cell, a stomach cancer cell, a uterine cancer cell, a lung cancer cell, a prostate cancer cell, an esophageal cancer cell, a colorectal cancer cell, a head and neck cancer cell, a kidney cancer cell, a pancreatic cancer cell, a sarcoma cell, a melanoma cell, or a hematologic cancer cell (lymphomas/leukemias/myeloma). The monoclonal antibody of the composition may be a recombinant single-chain variable antibody fragment, a Fv fragment, a Fab antibody fragment or be humanized.

Yet another embodiment comprises a method of inhibiting a cancer cell comprising contacting said cancer cell with an antibody that reacts immunologically with an epitope characterized by the primary sequence VDKSRWQQG (SEQ ID NO: 1). The cancer cell may be a breast cancer cell, an ovarian cancer cell, a stomach cancer cell, a uterine cancer cell, a lung cancer cell, a prostate cancer cell, an esophageal cancer cell, a colorectal cancer cell, a head and neck cancer cell, a kidney cancer cell, a pancreatic cancer cell, a sarcoma cell, a melanoma cell, or a hematologic cancer cell (lymphomas/leukemias/myeloma). Inhibiting comprises reducing growth of said cancer cell, reducing the viability of said cancer cell, reducing the invasiveness of said cancer cell or killing said cancer cell. The cancer cell may be a multidrug resistant cancer cell, metastaic and/or located in a living subject.

The contacting may be effected by systemic administration, by administration into a tumor vasculature, or by intratumoral administration. The method may further comprise multiple administrations of said antibody or composition to said subject. The subject may suffer from drug resistant, recurrent or metastatic cancer. The method may further comprise administering a second therapy to said subject, such as trastuzumab, trastuzumab-DM1 pertuzumab, cetuximab, panitumumab, rituximab, bevacizumab, edrecolomab, alemtuzumab, radiation, chemotherapy, hormonal therapy, toxin therapy, thymidine kinase therapy, cytokine therapy, immunotherapy or surgery. The subject may be a female with breast cancer having previously been treated with trastuzumab. The antibody may react immunologically with an epitope characterized by the primary sequence VDKSRWQQGNVFSCS-VMH (SEQ ID NO:2) and/or SFFLYSKLTVDKSRWQQG (SEQ ID NO:3). The antibody may be further defined as being produced by hybridoma cell line 992-18. The antibody may be an IgG antibody.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein:

(FIG. 1A) First mouse cohort. In the trastuzumab group (n=12), all responders had elevated average absorbance for TR-antibodies. All other mice had lower signal for serum TR-antibodies. (FIG. 1B) No significant mouse serum reactivity was found directed to the control human antibodies or fragments. Bars represent the average of absorbance at 1:40 dilution of serum in two independent experiments. (FIG. 1C) Average absorbance of TR-antibodies at 1:40 serum dilution in 16 mice treated with trastuzumab, according to time point of sample collection. No mouse had detectable anti-trastuzumab antibodies before treatment. (FIG. 1D) Average of tumor size over treatment period in the same mice. Anti-mouse IgG/HRP used as secondary antibody in all experiments. Abbreviations: PD, progressive disease; WT, wild type; Ab, antibody; Hu, human; DH, digested in house; CA, commercially available; WMOL, whole molecule; wk, week.

(FIG. 3A) Hybridomas were generated using B-cells obtained from the spleen of an FVB mouse transplanted with a HER2-overexpressing mammary gland tumor and treated with trastuzumab until complete response. Growing fusions were assayed by ELISA and dot blot testing for mouse IgG against trastuzumab and subsequently subcloned. One of the mouse anti-trastuzumab monoclonal antibodies produced was designated 992-18. (FIG. 3B) The 992-18 MAb was assayed against 72 overlapping trastuzumab synthetic peptides by dot blot assay, binding to the so-called D11 peptide. (FIG. 3C) Competition ELISA. Trastuzumab was immobilized on a plate and wells exposed to a constant concentration of 992-18 and decreasing concentration of D11 peptide. Secondary antibody was anti-mouse IgG Fc/HRP. Higher concentrations of D11 inhibit the binding of 992-18 to trastuzumab. (FIG. 3D) Mass spectrometry. Peptides bound to beads bearing the 992-18 MAb were detected using a Bruker Autoflex TOF mass spectrometer. Peptide B 10 is presented as an example of negative result in this assay. Abbreviations: Ab, antibody; MAbs, monoclonal antibodies; HER2, Human Epidermal Receptor 2; FVB, mouse strain (Friend leukemia virus B).

FIGS. 5A-D. The 992-18 MAb binds directly to breast cancer cell lines regardless of trastuzumab. (FIG. 5A) Trastuzumab bound to HER2 overexpressing cells, despite of the presence of 992-18 (first bar) or of its isotype control mIgG2b (fourth bar). Secondary antibody was anti-human IgG/HRP. (FIG. 5B) Binding of 992-18 or mIgG2b to SKBR3 cells, in the presence of different therapeutic antibodies. Secondary antibody was anti-mouse IgG/HRP. Binding of therapeutic antibodies to cells is not evaluated in this graph. 992-18 binds directly to SKBR3 cells (992-18 vs. mIgG2b; p=0.002), and despite the presence of therapeutic antibodies. FIGS. 5A and 5B results represent average of 4 wells per condition. (FIG. 5C) IFA of BT474 cells exposed to trastuzumab/Alexa$^{488}$ (green) and 992-18/Alexa$^{647}$ (red). (FIG. 5D) IFA of SKBR3 cells exposed to trastuzumab/Alexa$^{488}$ (green) and 992-18/Alexa$^{647}$ (red).

FIGS. 6A-B. Viability assay indicates that the 992-18 MAb is toxic to breast cancer cell lines. (FIG. 6A) Viability assay of BT474 cells exposed for 48 hr to 992-18 or isotype control (p=0.002). Trastuzumab was added for positive control. (FIG. 6B) Viability assay of SKBR3 cells exposed for 48 hr to 992-18 or isotype (p=0.0001). Abbreviations: TZB, trastuzumab; BEV, bevacizumab; RITUX, rituximab; Ab, antibody.

DETAILED DESCRIPTION OF THE INVENTION

Figure 1A:
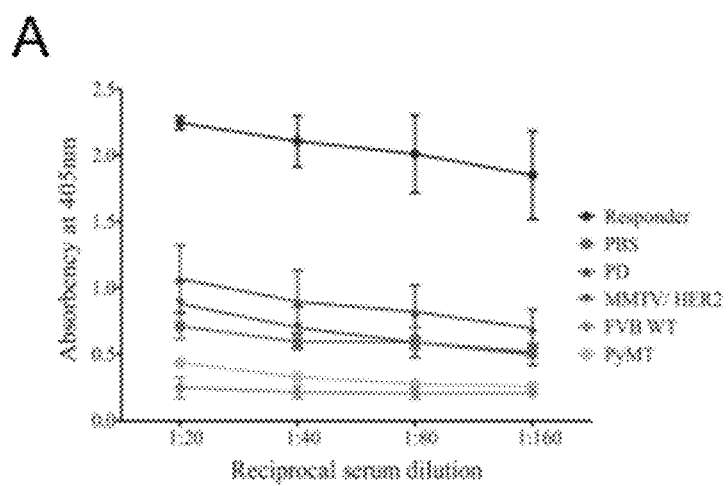
FIGS. 1A-D. Tumor responses to trastuzumab in mice are related to the presence of TR-antibodies in mouse serum.

Recombinant methodologies have allowed the production of monoclonal antibodies (MAbs) with higher percentages of human content to decrease antibody immunogenicity and reduce or eliminate the anti-antibody response. Trastuzumab (Tz) is a humanized MAb approved for treatment of HER2-overexpressing breast cancer. In assessing patients treated with Tz, the inventors previously detected anti-Tz antibodies in the serum of patients initially studied the effects of these antibodies on the response to Tz in a transgenic mouse model of breast cancer. All responders showed elevated anti-Tz antibodies, whereas in mice that had tumor progression anti-Tz levels were low or undetectable. These findings were confirmed in a second mouse cohort, in which anti-Tz antibodies were detected in responder mice as early as one week after starting treatment. MAbs produced by hybridomas stemming from spleen cells derived from responder mice bound Tz antibodies, arguing against the current understanding that an anti-xenoglobulin response to Tz would produce blocking antibodies. The inventor further sought to address if detectable anti-Tz antibodies would predict benefit from antibody therapy in patients with HER2+ breast cancer. With a median follow-up of 36 months, 14 patients had had disease progression while on Tz plus vaccine. Analysis revealed that higher anti-Tz F(ab')2 antibodies were significantly associated with lower risk of disease progression.

In studies reported here, fine specificity analysis confirms the presence of a human polyclonal response to Tz, directed to epitopes present in both its Fc and Fab regions. Response to Tz was significantly associated with the presence of anti-Tz antibodies in serum, while in patients with stage IV breast cancer treated with Tz, the presence of anti-Tz F(ab')2 antibodies was associated with longer PFS. MAbs produced by hybridomas stemming from spleen B-cells derived from responder mice bound trastuzumab. One of these MAbs was called 992-18. Its cognate epitope on trastuzumab was defined. The specificity of this antibody indicates that it, along with the polyclonal response epitopes, correlates with both Fc and Fab regions from the therapeutic antibody, and in several cases includes antibodies react with the same cognate epitope of 992-18. Therefore the 992-18 MAb was validated for subsequent mechanistic studies.

Additional data presented here support the treatment of patients with TR-antibodies for their anti-tumor properties. The resultant humoral response to trastuzumab exposure is potentially capable of producing antibodies that directly target cancer cells. Thus, the inventors provide data supporting the use of a mAb as a "vaccine-like" therapy. This concept is especially relevant for the development of new anti-tumoral antibodies and of biosimilars. These and other aspects of the invention are described in detail below.

I. Definitions

As used herein the specification, "a" or "an" may mean one or more. As used herein in the claim(s), when used in conjunction with the word "comprising," the words "a" or "an" may mean one or more than one. As used herein "another" may mean at least a second or more. Some embodiments of the invention may consist of or consist essentially of one or more elements, method steps, and/or methods of the invention. It is contemplated that any method or composition described herein can be implemented with respect to any other method or composition described herein.

The term "antigen" or "immunogen" as used herein is defined as a molecule that provokes an immune response when it is introduced into a subject or produced by a subject (tumor antigens arise by the cancer development itself). This immune response may involve either antibody production, or the activation of specific immunologically-competent cells, or both. An antigen can be derived from organisms, subunits of proteins/antigens, killed or inactivated whole cells or lysates, although in the present invention the antigen is a tumor antigen on the surface of a cancer cell. Commonly, an antigen is a molecule that causes the subject in which it is introduced to produce antibodies that specifically recognize the antigen. The part of the antigen with which the antibody interacts is termed an "epitope" or "antigenic determinant". A skilled artisan realizes that any macromolecule, including virtually all proteins or peptides, can serve as antigens. Furthermore, antigens can be derived from recombinant or genomic DNA. A skilled artisan realizes that any DNA that contains nucleotide sequences or partial nucleotide sequences of a pathogenic genome or a gene or a fragment of a gene for a protein that elicits an immune response results in synthesis of an antigen.

The term "antigenic" and "immunogenic" as used herein describe a structure that is an antigen. These terms can be used interchangeably.

The term "antibody" as used herein refers to an immunoglobulin molecule, which is able to specifically bind to a specific epitope on an antigen. As used herein, an antibody is intended to refer broadly to any immunologic binding agent such as IgG, IgM, IgA, IgD and IgE. Antibodies can be intact immunoglobulins derived from natural sources or from recombinant sources and can be immunoactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies and fusion proteins containing antibody-derived antigen binding domains (Harlow and Lane, 1988; Bird et al., 1988).

As used herein, the term "pharmaceutically or pharmacologically acceptable" refers to molecular entities and compositions that do not produce adverse, allergic, or other untoward reactions when administered to an animal or a human.

The term "pharmaceutically acceptable carrier" or "pharmaceutically acceptable excipient" or "physiologically acceptable carrier" as used herein includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, dyes, such like materials and combinations thereof, as would be known to one of ordinary skill in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated. The carrier may not produce an adverse, allergic or other untoward reaction when administered to an animal, such as, for example, a human, as appropriate. These terms can be used interchangeably.

The term "subject" or "individual," as used herein refers to animals, including mammals. More specifically, mammals include, but are not limited to rats, mice, rabbits, cats, dogs, monkeys and humans. These terms can be used interchangeably.

II. Embodiments of the Present Invention

Human epidermal growth factor receptor-2 (HER2; also called ErbB2) is a cell-surface protein involved in cell development. Activation of HER2 in cancer cells accelerates many cellular processes associated with tumor formation, including cell proliferation, angiogenesis, adhesion, and resistance to chemotherapy. About 25% of breast cancers overexpress HER2, which is found on their cell surface. Trastuzumab (see, for example, U.S. Pat. No. 6,800,738) is a therapeutic monoclonal Ab that targets tumor cells that overexpress HER2 and is used to treat HER2-positive breast cancer. In patients previously treated with cytotoxic chemotherapy whose tumors overexpress HER2, administration of Trastuzumab as a single agent results in a response rate of 25%.

Immunity against HER2 is present in about 30-50% of patients with HER2-positive breast cancer. According to Jerne's immune network hypothesis, if there is an immune response with antibody (Ab1) production, there may be a regulatory response, with production of a second antibody (Ab2) that binds to and interacts with Ab1. Little is known about the presence of endogenous antibody (Ab) directed to therapeutic anti-HER2 Abs in patients or in animals.

The present inventors have detected endogenous antibogies that react with anti-HER2 Abs in the serum of untreated patients suffering from HER2-positive and HER2-negative breast cancer, but rarely in healthy donors. Additionally, in a breast cancer murine model, the presence of anti-anti-HER2 or anti-anti-EGFR endogenous antibodies in the serum of mice was directly related to better tumor response to standard immunotherapeutic treatment.

Therefore, it is contemplated that endogenous antibodies (e.g., Ab2), present in humans, that interact with therapeutic anti-HER2 (e.g., Herceptin/Trastuzumab) or anti-EGFR (e.g., Erbitux/Cetuximab) antibodies may be useful in one or more different settings: (1) biomarkers for cancer diagnosis; (2) biomarkers for cancer prognosis; (3) biomarker for treatment selection in personalized medicine; and/or (4) therapy when used individually, or in combination with standard therapy for cancer.

III. Monoclonal Antibodies for Immunotherapy

The present invention provides antibodies to be used as immunotherapy for hyperproliferative diseases and disorders. Monoclonal antibodies of the present invention are immunogically reactive with anti-tumor antigen antibodies and are compatible with the human immune system. Thus, in one aspect, the invention is directed to a human or humanized monoclonal monoclonal antibody immunoreactive with anti-tumor antigen antibodies wherein the framework regions (FRs) of the variable regions of said antibody and the constant regions of said antibody are compatible with the human immune system. More specifically, the monoclonal antibody or immunoreactive fragment thereof, is immunoreactive with anti-tumor antigen antibodies and compatible with the human immune system, wherein the framework regions (FRs) of the variable regions of said antibody or fragment and any constant regions of said antibody or fragment are of human origin.

Thus, as used herein the term "humanized" is directed to antibodies or fragments immunospecific for anti-tumor antigen antibodies that have sufficient human characteristics so that their immunogenicity in human systems is lowered with respect to the corresponding antibodies derived from other species. Thus, the humanized antibodies or immunoreactive fragments of the invention are compatible with the human immune system. By "compatible with the human immune system" is meant that the antibodies or fragments of the invention do not elicit a substantial immune response when administered to humans as compared to unmodified forms of nonhuman antibodies containing the same complementarity-determining regions (CDRs). Eliciting an immune response is clearly undesirable as antibodies raised against therapeutically administered materials undermine the effectiveness of the administered materials and in addition may provoke unwanted side-effects due to stimulation of the immune system per se. While the antibodies and fragments of the invention may not, of course, be completely neutral with respect to an immune response in a specific individual, their effect on the immune system of an individual will be substantially less than that elicited by corresponding nonhuman antibodies in their unmodified forms.

Yet further, as used herein, the term "fully human antibody" or "fully humanized antibody" refers to antibodies or fragments immunospecific for human anti-tumor antigen antibodies that have relatively no CDR or FR residues substituted from analogous sites in nonhuman species. Thus, the human variable domain is intact.

As discussed herein, minor variations in the amino acid sequences of antibodies or immunoglobulin molecules are contemplated as being encompassed by the humanized antibodies of the present invention, providing that the variations in the amino acid sequence maintain at least 75%, more preferably at least 80%, 90%, 95%, and most preferably 99% homology to the human variable domain. Specifically, in the present invention if the humanized antibody maintains at least 95% and most preferably 99% homology to the human variable domain, then the humanized antibody is considered to be fully humanized.

In particular, the variations that may be contemplated are conservative amino acid replacements. Conservative replacements are those that take place within a family of amino acids that are related in their side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=lycine, asparagine, glutamine, cysteine, serine, threonine, tyrosine. More particular families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Fragments or analogs of antibodies or immunoglobulin molecules can be readily prepared by those of ordinary skill in the art. Particular amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known (Bowie et al., 1991).

Particular amino acid substitutions are those such as follows: (1) reduce susceptibility to proteolysis, (2) reduce susceptibility to oxidation, (3) alter binding affinity for forming protein complexes, (4) alter binding affinities, and (4) confer or modify other physiocochemical or functional properties of such analogs. Analogs can include various mutations of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence).

IV. Antibody Preparation

Yet further, the antibodies of the present invention that react immunologically with anti-tumor antigen antibodies may be produced using standard procedures that are well known and used in the art.

A. Monoclonal Antibodies

The methods for generating monoclonal antibodies (MAbs) generally begin along the same lines as those for preparing polyclonal antibodies. Rodents such as mice and rats are particular animals, however, the use of rabbit, sheep, goat, monkey cells also is possible. The use of rats may provide certain advantages (Goding, 1986), but mice are used, with the BALB/c mouse being most routinely used and generally gives a higher percentage of stable fusions.

Monoclonal antibodies are obtained from a population of substantially homogeneous antibodies, i.e., the individual antibodies comprising the population are identical except for possible naturally-occurring mutations that may be present in minor amounts. Thus, the modifier "monoclonal" indicates the character of the antibody as not being a mixture of discrete antibodies. Methods for generating monoclonal antibodies are described elsewhere herein.

B. Humanized Antibodies

Methods for humanizing non-human antibodies are well known in the art. Generally, a humanized antibody has one or more amino acid residues introduced into it from a source, which is non-human. These non-human amino acid residues are often referred to as "import" residues, which are typically taken from an "import" variable domain. Humanization can be essentially performed following the method of Winter and co-workers (Jones et al., 1986; Riechmann et al., 1988; Verhoeyen et al., 1988), by substituting rodent CDRs or CDR sequences for the corresponding sequences of a human antibody. Accordingly, such "humanized" antibodies are chimeric antibodies wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

It may be beneficial that antibodies be humanized with retention of high affinity for the antigen and other favorable biological properties. To achieve this goal, according to a particular method, humanized antibodies are prepared by a process of analysis of the parental sequences and various conceptual humanized products using three-dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e. the analysis of residues that influence the ability of the candidate immunoglobulin to bind its antigen.

C. Human Antibodies

Human monoclonal antibodies can be made by the hybridoma method. Human myeloma and mouse-human heteromyeloma cell lines for the production of human monoclonal antibodies have been described (Kozbor, 1984; U.S. Pat. No. 6,150,584, which is incorporated herein by reference).

It is now possible to produce transgenic animals (e.g., mice) that are capable, upon immunization, of producing a repertoire of human antibodies in the absence of endogenous immunoglobulin production. For example, it has been described that the homozygous deletion of the antibody heavy chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge (Jakobovits et al., 1993).

Alternatively, the phage display technology (McCafferty et al., 1990) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle.

V. Immunotherapy Treatments

A. Treatment of Hyperproliferative Diseases

In certain embodiments, a hyperproliferative disease may be treated by administering to a subject an effective amount of antibodies that react immunologically with an epitope comprising VDKSRWQQG (SEQ ID NO: 1), and optionally with anti-tumor antigen antibodies and/or cancer cells. The subject may be a mammal, and more particularly, is a human. A hyperproliferative disease is further defined as cancer. In still further embodiments, the cancer is melanoma, non-small cell lung, small-cell lung, lung, leukemia, hepatocarcinoma, retinoblastoma, astrocytoma, glioblastoma, gum, tongue, neuroblastoma, head, neck, breast, pancreatic, prostate, renal, bone, testicular, ovarian, mesothelioma, cervical, gastrointestinal, lymphoma, stomach, uterine, brain, colon, sarcoma or bladder.

The cancer may include a tumor comprised of tumor cells. For example, tumor cells may include, but are not limited to melanoma cell, a bladder cancer cell, a breast cancer cell, a lung cancer cell, a colon cancer cell, a prostate cancer cell, a liver cancer cell, a pancreatic cancer cell, a stomach cancer cell, a testicular cancer cell, a brain cancer cell, an ovarian cancer cell, a lymphatic cancer cell, a skin cancer cell, a brain cancer cell, a bone cancer cell, or a soft tissue cancer cell.

In a particular embodiment of the present invention, antibodies that react immunologically with VDKSRWQQG (SEQ ID NO: 1) are administered in an effective amount to decrease, reduce, inhibit or abrogate the growth of cancer, including of a solid tumor. Examples of solid tumors that can be treated according to the invention include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

Yet further, hyperproliferative diseases that are most likely to be treated in the present invention are those that metastasize. It is understood by those in the art that metastasis is the spread of cells from a primary tumor to a noncontiguous site, usually via the bloodstream or lymphatics, which results in the establishment of a secondary tumor growth. Examples of hyperproliferative diseases contemplated for treatment include, but are not limited to cancers including melanoma, bladder, non-small cell lung, small cell lung, lung, hepatocarcinoma, retinoblastoma, astrocytoma, glioblastoma, neuroblastoma, head, neck, breast, pancreatic, gum, tongue, prostate, renal, uterine, stomach, bone, testicular, ovarian, mesothelioma, cervical, gastrointestinal lymphoma, brain, or colon cancer and any other hyperproliferative diseases that may be treated by administering an antibody that reacts immunologically with an anti-tumor antigen antibody.

B. Treatment Regimens

Treatment regimens may vary as well, and often depend on tumor type, tumor location, disease progression, and health and age of the patient. Obviously, certain types of tumor will require more aggressive treatment, while at the same time, certain patients cannot tolerate more taxing protocols. The clinician will be best suited to make such decisions based on the known efficacy and toxicity (if any) of the therapeutic formulations.

In certain aspects, patients to be treated will have adequate bone marrow function (defined as a peripheral absolute granulocyte count of >2,000/mm$^3$ and a platelet count of 100,000/mm$^3$), adequate liver function (bilirubin<1.5 mg/dl) and adequate renal function (creatinine<1.5 mg/dl).

As used herein the term "effective amount" is defined as an amount of the agent that will decrease, reduce, inhibit or otherwise abrogate the growth of a cancer cell, induce apoptosis, inhibit angiogenesis of a tumor cell, inhibit metastasis, or induce cytotoxicity in cells. Thus, an effective amount is an amount sufficient to detectably and repeatedly ameliorate, reduce, minimize or limit the extent of the disease or its symptoms. More rigorous definitions may apply, including elimination, eradication or cure of disease.

To kill cells, inhibit cell growth, inhibit metastasis, decrease tumor or tissue size and otherwise reverse or reduce the malignant phenotype of tumor cells, using the methods and compositions of the present invention, one would generally contact anti-tumor antigen antibodies with an antibody that reacts immunologically thereto. The routes of administration will vary, naturally, with the location and nature of the lesion, and include, e.g., intradermal, transdermal, parenteral, intravenous, intramuscular, intranasal, subcutaneous, percutaneous, intratracheal, intraperitoneal, intratumoral, perfusion, lavage, direct injection, and oral administration and formulation.

In the case of surgical intervention, the present invention may be used preoperatively, to render an inoperable tumor subject to resection. Alternatively, the present invention may be used at the time of surgery, and/or thereafter, to treat residual or metastatic disease. For example, a resected tumor bed may be injected or perfused with a formulation comprising an antibody that reacts immunologically with an anti-tumor antigen antibody. The perfusion may be continued post-resection, for example, by leaving a catheter implanted at the site of the surgery. Periodic post-surgical treatment also is envisioned.

Continuous administration also may be applied where appropriate, for example, where a tumor is excised and the tumor bed is treated to eliminate residual, microscopic disease. Delivery via syringe or catherization is in particular contemplated. Such continuous perfusion may take place for a period from about 1-2 hours, to about 2-6 hours, to about 6-12 hours, to about 12-24 hours, to about 1-2 days, to about 1-2 wk or longer following the initiation of treatment. Generally, the dose of the therapeutic composition via continuous perfusion will be equivalent to that given by a single or multiple injections, adjusted over a period of time during which the perfusion occurs. It is further contemplated that limb perfusion may be used to administer therapeutic compositions of the present invention, particularly in the treatment of melanomas and sarcomas.

In certain embodiments, the tumor being treated may not, at least initially, be resectable. Treatments with therapeutic antibodies may increase the resectability of the tumor due to shrinkage at the margins or by elimination of certain particularly invasive portions. Following treatments, resection may be possible. Additional treatments subsequent to resection will serve to eliminate microscopic residual disease at the tumor site.

A typical course of treatment, for a primary tumor or a post-excision tumor bed, will involve multiple doses. Typical primary tumor treatment involves a 6 dose application over a two-week period. The two-week regimen may be repeated one, two, three, four, five, six or more times. During a course of treatment, the need to complete the planned dosings may be re-evaluated.

The treatments may include various "unit doses." Unit dose is defined as containing a predetermined-quantity of the therapeutic composition. The quantity to be administered, and the particular route and formulation, are within the skill of those in the clinical arts. A unit dose need not be administered as a single injection but may comprise continuous infusion over a set period of time.

C. Treatment Regimen for Breast Cancer

It is envisioned that breast cancer, as only an exemplary cancer for treatment with the present invention, may be treated by employing the antibody treatment of the present invention. For example, antibodies that react immunologically with anti-tumor antigen antibodies may be employed at a starting dose of 1-3 mg/kg. Dosing may be every 3 weeks for 4 cycles (total=12 weeks), at which time response may also be determined. If no dose-limiting toxicity is observed after 2 cycles, then the next dosing level may be initiated according to standard dose-escalation algorithms (i.e., 3 mg/kg, 6 mg/kg, 9 mg/kg, 13.5 mg/kg, etc.).

In addition to toxicity and response data, tissue and serum samples are collected pre-therapy and post-therapy (after 2 and 4 cycles) to provide the basis for studies on intermediate biomarkers involved in angiogenesis and invasion and to evaluate whether these markers can predict response to treatment. To assess for alterations in blood flow, in situ, blood flow patterns are assessed in real time using 3-D re-constructions of high resolution cutaneous Doppler ultrasound examinations of accessible tumors pre-therapy and after 2 to 4 cycles.

VI. Combination Treatments

In some embodiments of the invention, it may be desirable to combine compositions for administration to the subject, particularly combining antibodies that react immunologically with VDKSRWQQG (SEQ ID NO: 1) and anti-tumor antigen antibodies themselves. Yet further, it may be desirable to combine either or both of these antibodies with other agents effective in the treatment of hyperproliferative disease, such as anti-cancer agents, or with surgery. It is also contemplated that antibodies that react immunologically with VDKSR-WQQG (SEQ ID NO: 1) may be administered in combination with an additional "standard" anti-cancer agent. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, reducing invasiveness, promoting an immune response against cancer cells or a tumor, preventing or inhibiting the progression of cancer, or increasing the lifespan of a subject with cancer. Anti-cancer agents include biological agents (biotherapy), hormonal agents, toxins, chemotherapy agents, and radiotherapy agents. More generally, these other compositions would be provided in a combined amount effective to kill or inhibit proliferation of the cell. This process may involve contacting the cells with the antibodies of the present invention and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the antibodies and the other includes the second agent(s).

In some embodiments, the antibodies that react immunologically with VDKSRWQQG (SEQ ID NO: 1) and another agent may act additively or synergistically with each other.

Alternatively, the antibodies of the present invention may precede or follow the other anti-cancer agent treatment by intervals ranging from minutes to weeks. In embodiments where the other anti-cancer agent and antibodies are applied separately to the cell, one would generally ensure that a significant period of time did not expire between the time of each delivery, such that the agent and antibodies would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Various combinations may be employed, antibodies of the present invention is "A" and the secondary agent, such as radio- or chemotherapy, is "B", or antibodies that react immunologically with anti-tumor antigen antibodies (including trastuzumab) is "A" and the anti-tumor antigen antibodies themselves are "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of the immunotherapy of the present invention to a patient will follow general protocols for the administration of chemotherapeutics. It is expected that the treatment cycles would be repeated as necessary. It also is contemplated that various standard therapies, as well as surgical intervention, may be applied in combination with the described hyperproliferative cell therapy.

A. Chemotherapy

Cancer therapies also include a variety of chemical based treatments. Some examples of chemotherapeutic agents include antibiotic chemotherapeutics such as Doxorubicin, Daunorubicin, Adriamycin, Mitomycin (also known as mutamycin and/or mitomycin-C), Actinomycin D (Dactinomycin), Bleomycin, Plicomycin, plant alkaloids such as Paclitaxel, Docetaxel, Vincristine, Vinblastine, miscellaneous agents such as Cisplatin (CDDP), etoposide (VP16), Tumor Necrosis Factor, and alkylating agents such as, Carmustine, Melphalan (also known as alkeran, L-phenylalanine mustard, phenylalanine mustard, L-PAM, or L-sarcolysin, is a phenylalanine derivative of nitrogen mustard), Cyclophosphamide, Chlorambucil, Busulfan (also known as myleran), and Lomustine.

Some examples of other agents include, but are not limited to, Carboplatin, Procarbazine, Mechlorethamine, Camptothecin, Ifosfamide, Nitrosurea, Etoposide (VP 16), Tamoxifen, Raloxifene, Toremifene, Idoxifene, Droloxifene, TAT-59, Zindoxifene, Trioxifene, ICI 182,780, EM-800, Estrogen Receptor Binding Agents, Gemcitabien, Navelbine, Farnesyl-protein transferase inhibitors, Transplatinum, 5-Fluorouracil, hydrogen peroxide, and Methotrexate, Temazolomide (an aqueous form of DTIC), Mylotarg, Dolastatin-10, Bryostatin, or any analog or derivative variant of the foregoing.

B. Radiotherapeutic Agents

Radiotherapeutic agents and factors include radiation and waves that induce DNA damage for example, γ-irradiation, X-rays, UV-irradiation, microwaves, electronic emissions, radioisotopes, and the like. Therapy may be achieved by irradiating the localized tumor site with the above described forms of radiations. It is most likely that all of these factors effect a broad range of damage DNA, on the precursors of DNA, the replication and repair of DNA, and the assembly and maintenance of chromosomes.

Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

C. Anti-Tumor Antibodies

Another combination therapy relates to the use of anti-tumor antigen antibodies. Of particular interest will be the use of trastuzumab. Trastuzumab (Herceptin®) is a monoclonal antibody that interferes with the HER2/neu receptor. The HER receptors are proteins that are embedded in the cell membrane and communicate molecular signals from outside the cell to inside the cell, and turn genes on and off. The HER proteins regulate cell growth, survival, adhesion, migration, and differentiation—functions that are amplified or weakened in cancer cells. In some cancers, notably some breast cancers, HER2 is over-expressed, and, among other effects, causes breast cells to reproduce uncontrollably.

Trastuzumab binds selectively to the HER2 protein. When it binds to defective HER2 proteins, the HER2 protein no longer causes cells in the breast to reproduce uncontrollably. This increases the survival of people with cancer. However, cancers usually develop resistance to trastuzumab. The original studies of trastuzumab showed that it improved survival in late-stage (metastatic) breast cancer, but there is controversy over whether trastuzumab is effective in earlier stage cancer. Trastuzumab is also being studied for use with other cancers. It has been used with some success in women with uterine papillary serous carcinomas that overexpress HER2/neu and in patients with metastatic gastric and gastroesophageal junction HER2-positive adenocarcinomas.

Other anti-tumor antibodies include but are not limited to trastuzumab-DM 1, pertuzumab, cetuximab, panitumumab, rituximab, bevacizumab, edrecolomab, or alemtuzumab.

D. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

E. Gene Therapy

In yet another embodiment, gene therapy in conjunction with the combination therapy using the antibody compounds described in the invention are contemplated. A variety of proteins are encompassed within the invention, some of which are described below. Various genes that may be targeted for gene therapy of some form in combination with the present invention are known in the art, including p53, BRCA1, and/or BRCA2, for example.

VII. Immunological Reagents

In certain aspects of the invention, one or more antibodies are employed for either therapeutic, prognostic, and/or diagnostic embodiments. Antibodies include any type of antibody, and specifically refer to antibodies that react immunologically with anti-tumor antigen antibodies and/or anti-tumor antigens, in certain embodiments. In particular, these antibodies may be used in various diagnostic or therapeutic applications, described herein below.

As used herein, the term "antibody" is intended to refer broadly to any immunologic binding agent such as IgG, IgM, IgA, IgD and IgE. The term "antibody" is used to refer to any antibody-like molecule that has an antigen binding region, and includes antibody fragments such as Fab', Fab, F(ab')2, single domain antibodies (DABs), Fv, scFv (single chain Fv), and the like. The techniques for preparing and using various antibody-based constructs and fragments are well known in the art. Means for preparing and characterizing antibodies are also well known in the art (see, e.g., Antibodies: A Laboratory Manual, Cold Spring Harbor Laboratory, 1988; incorporated herein by reference).

Monoclonal antibodies (MAbs) are recognized to have certain advantages, e.g., reproducibility and large-scale production. The invention thus provides monoclonal antibodies of the human, murine, monkey, rat, hamster, rabbit and even chicken origin. Due to the ease of preparation and ready availability of reagents, murine monoclonal antibodies will often be utilized.

However, "humanized" antibodies are also contemplated, as are chimeric antibodies from mouse, rat, or other species, bearing human constant and/or variable region domains, bispecific antibodies, recombinant and engineered antibodies and fragments thereof. Methods for the development of antibodies that are "custom-tailored" to the patient's disease are likewise known and such custom-tailored antibodies are also contemplated.

A. Antibody Conjugates

The present invention further provides antibody conjugates. In order to increase the efficacy of antibody molecules as diagnostic or therapeutic agents, one may link or covalently bind or complex to an antibody. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radio-labeled nucleotides, antiviral agents, chelating agents, cytokines, growth factors, and oligo- or polynucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin.

Any antibody of sufficient selectivity, specificity or affinity may be employed as the basis for an antibody conjugate. Such properties may be evaluated using conventional immunological screening methodology known to those of skill in the art. Sites for binding to biological active molecules in the antibody molecule, in addition to the canonical antigen binding sites, include sites that reside in the variable domain that can bind pathogens, B-cell superantigens, the T cell co-receptor CD4 and the HIV-1 envelope (Sasso et al., 1989; Shorki et al., 1991; Silvermann et al., 1995; Cleary et al., 1994; Lenert et al., 1990; Berberian et al., 1993; Kreier et al., 1991). In addition, the variable domain is involved in antibody self-binding (Kang et al., 1988), and contains epitopes (idiotypes) recognized by anti-antibodies (Kohler et al., 1989).

Certain examples of antibody conjugates are those conjugates in which the antibody is linked to a detectable label. "Detectable labels" are compounds and/or elements that can be detected due to their specific functional properties, and/or chemical characteristics, the use of which allows the antibody to which they are attached to be detected, and/or further quantified if desired. Another such example is the formation of a conjugate comprising an antibody linked to a cytotoxic or anti cellular agent, and may be termed "immunotoxins."

Antibody conjugates are used as diagnostic agents. Antibody diagnostics generally fall within two classes, those for use in in vitro diagnostics, such as in a variety of immunoassays, and/or those for use in vivo diagnostic protocols, generally known as "antibody directed imaging."

Many appropriate imaging agents are known in the art, as are methods for their attachment to antibodies (see, for e.g., U.S. Pat. Nos. 5,021,236; 4,938,948; and 4,472,509, each incorporated herein by reference). The imaging moieties used can be paramagnetic ions; radioactive isotopes; fluorochromes; NMR-detectable substances; X-ray imaging.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III). Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$ rhenium$^{188}$, $^{75}$selenium, $^{35}$sulphur, technicium$^{99m}$ and/or yttrium$^{90}$. $^{125}$I is often being commonly used in certain embodiments, and technicium99m and/or indium$^{111}$ are also often used due to their low energy and suitability for long range detection. Radioactively labeled monoclonal antibodies of the present invention may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the invention may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCl$_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugates contemplated in the present invention are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241; each incorporated herein by reference.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter & Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; and Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such as described in U.S. Pat. Nos. 4,472,509 and 4,938,948, each incorporated herein by reference). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

B. Immunodetection Methods

In still further embodiments, the present invention concerns immunodetection methods for binding, purifying, removing, quantifying and/or otherwise generally detecting biological components such as antibodies that react immunologically with anti-tumor antigen antibodies and/or the anti-tumor antigen antibodies themselves. Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle and Ben-Zeev, 1999; Gulbis and Galand, 1993; De Jager et al., 1993; and Nakamura et al., 1987, each incorporated herein by reference.

In general, the immunobinding methods include obtaining a sample suspected of containing antibodies that react immunologically with anti-tumor antigen antibodies, and contacting the sample with a first antibody that reacts immunologically with anti-tumor antigen antibodies antibody in accordance with the present invention, as the case may be, under conditions effective to allow the formation of immunocomplexes.

These methods include methods for purifying an antibody that reacts immunologically with anti-tumor antigen antibodies from organelle, cell, tissue or organism's samples. In these instances, the antibody removes the antigenic antibodies that react immunologically with anti-tumor antigen antibodies message, protein, polypeptide and/or peptide component from a sample. The antibody will preferably be linked to a solid support, such as in the form of a column matrix, and the sample suspected of containing the antibodies that react immunologically with anti-tumor antigen antibodies component will be applied to the immobilized antibody. The unwanted components will be washed from the column, leaving the antigen immunocomplexed to the immobilized antibody to be eluted.

The immunobinding methods also include methods for detecting and quantifying the amount of an antigen component in a sample and the detection and quantification of any immune complexes formed during the binding process. Here, one would obtain a sample suspected of containing an antigen, and contact the sample with an antibody against the antibodies that react immunologically with anti-tumor antigen antibodies produced antigen, and then detect and quantify the amount of immune complexes formed under the specific conditions.

In terms of antigen detection, the biological sample analyzed may be any sample that is suspected of containing an antigen, such as, for example, a tissue section or specimen, a homogenized tissue extract, a cell, an organelle, separated and/or purified forms of any of the above antigen-containing compositions, or even any biological fluid that comes into contact with the cell or tissue, including blood and/or serum, although tissue samples or extracts may be used.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any antibodies that react immunologically with anti-tumor antigen antibodies present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection designed by Charles Cantor uses two different antibodies. A first step biotinylated, monoclonal or polyclonal antibody is used to detect the target antigen(s), and a second step antibody is then used to detect the biotin attached to the complexed biotin. In that method the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

The immunodetection methods of the present invention have evident utility in the diagnosis and prognosis of conditions such as cancer wherein a specific tumor antigen is expressed, and wherein antibodies exist that react immunologically to an anti-tumor antigen antibody. Here, a biological and/or clinical sample suspected of containing a specific disease associated antibody is used. However, these embodiments also have applications to non-clinical samples, such as in the titering of antigen or antibody samples, for example in the selection of hybridomas.

In the clinical diagnosis and/or monitoring of patients with various forms a disease, such as, for example, cancer, the detection of a cancer specific antibodies that react immunologically with anti-tumor antigen antibodies, and/or an alteration in the levels of antibodies that react immunologically with anti-tumor antigen antibodies, in comparison to the levels in a corresponding biological sample from a normal subject is indicative of a patient with cancer. However, as is known to those of skill in the art, such a clinical diagnosis would not necessarily be made on the basis of this method in isolation. Those of skill in the art are very familiar with differentiating between significant differences in types and/or amounts of biomarkers, which represent a positive identification, and/or low level and/or background changes of biomarkers. Indeed, background expression levels are often used to form a "cut-off" above which increased detection will be scored as significant and/or positive. Of course, the antibodies of the present invention in any immunodetection or therapy known to one of ordinary skill in the art.

As detailed above, immunoassays, in their most simple and/or direct sense, are binding assays. Certain immunoassays are the various types of enzyme linked immunosorbent assays (ELISAs) and/or radioimmunoassays (RIA) known in the art. Immunohistochemical detection using tissue sections is also particularly useful. However, it will be readily appreciated that detection is not limited to such techniques, and/or western blotting, dot blotting, FACS analyses, and/or the like may also be used.

In some aspects of the invention, there are ELISA/trastuzumab assays, including in kits, to test samples of subjects that are starting treatment with trastuzumab, to predict response. This may be considered is a new use for a known Ab. In addition, there may be an ELISA/therapeutic Abs kit, to test all at once. In particular, exemplary mAbs that concern the invention include trastuzuman (Herceptin®), cetuximab, (C225 or Erbitux®), rituximab (Rituxan® or Mabthera), Bevacizumab (Avastin®), Edrecolomab (Panorex®), and Alemtuzumab (Campath®).

In one exemplary ELISA, the anti-ORF message and/or anti-ORF translated product antibodies of the invention are immobilized onto a selected surface exhibiting protein affinity, such as a well in a polystyrene microtiter plate. Then, a test composition suspected of containing the antigen, such as a clinical sample, is added to the wells. After binding and/or washing to remove non-specifically bound immune complexes, the bound antigen may be detected. Detection is generally achieved by the addition of another anti-ORF message and/or anti-ORF translated product antibody that is linked to a detectable label. This type of ELISA is a simple "sandwich ELISA." Detection may also be achieved by the addition of a second anti-ORF message and/or anti-ORF translated product antibody, followed by the addition of a third antibody that has binding affinity for the second antibody, with the third antibody being linked to a detectable label.

In another exemplary ELISA, the samples suspected of containing the antigen are immobilized onto the well surface and/or then contacted with the anti-ORF message and/or anti-ORF translated product antibodies of the invention. After binding and/or washing to remove non-specifically bound immune complexes, the bound anti-ORF message and/or anti-ORF translated product antibodies are detected. Where the initial anti-ORF message and/or anti-ORF translated product antibodies are linked to a detectable label, the immune complexes may be detected directly. Again, the immune complexes may be detected using a second antibody that has binding affinity for the first anti-ORF message and/or anti-ORF translated product antibody, with the second antibody being linked to a detectable label.

Another ELISA in which the antigens are immobilized, involves the use of antibody competition in the detection. In this ELISA, labeled antibodies against an antigen are added to the wells, allowed to bind, and/or detected by means of their label. The amount of an antigen in an unknown sample is then determined by mixing the sample with the labeled antibodies against the antigen during incubation with coated wells. The presence of an antigen in the sample acts to reduce the amount of antibody against the antigen available for binding to the well and thus reduces the ultimate signal. This is also appropriate for detecting antibodies against an antigen in an unknown sample, where the unlabeled antibodies bind to the antigen-coated wells and also reduces the amount of antigen available to bind the labeled antibodies.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A particular washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

The antibodies of the present invention may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and/or is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in 70° C. isopentane; cutting the plastic capsule and/or removing the frozen cylinder of tissue; securing the tissue cylinder on a cryostat microtome chuck; and/or cutting 25-50 serial sections.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections.

VIII. Pharmaceutical Formulations and Delivery

The pharmaceutical or antibody compositions disclosed herein may be administered parenterally, intravenously, intradermally, intramuscularly, transdermally or even intraperitoneally as described in U.S. Pat. Nos. 5,543,158, 5,641,515 and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intratumoral and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, specific methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

IX. Kits of the Invention

Any of the antibodies of the invention may be comprised in a kit. The kit may comprise a suitably aliquoted antibody that reacts immunologically with VDKSRWQQG (SEQ ID NO: 1), wash solutions, blocking agents, reporter molecules, means for detecting the reporter molecule, a suitable solid surface support means such as a microplate and/or additional reagents. The components of the kits may be packaged either in aqueous media or in lyophilized form. When reagents and/or components are provided as a dry powder, the powder can be reconstituted by the addition of a suitable solvent. It is envisioned that the solvent may also be provided. Additionally, a microplate or other suitable solid surface support means may be provided pre-bound to one or more antibody that reacts immunologically with VDKSRWQQG (SEQ ID NO: 1).

The container means of the kits will generally include at least one vial, test tube, flask, bottle, syringe or other container means, into which a component may be placed, and preferably, suitably aliquoted. Where there is more than one component in the kit, the kit also will generally contain a second, third or other additional containers into which the additional components may be separately placed. However, various combinations of components may be comprised in a vial. The kits of the present invention also will typically include a means for containing the reagent vials and other kit components in close confinement for commercial sale. Such containers may include injection or blow molded plastic containers into which the desired vials are retained.

In specific embodiments, the kit comprises an ELISA assay with any antibodies that react immunologically with VDKSRWQQG (SEQ ID NO: 1).

Irrespective of the number or type of containers, the kits of the invention may also comprise, or be packaged with, an instrument for assisting with the injection/administration or placement of the immunogenic composition within the body of an animal. Such an instrument may be a syringe, pipette, forceps, or any such medically approved delivery vehicle.

X. EXAMPLES

The following examples are included to demonstrate particular embodiments of the invention. It should be appreciated by those of skill in the art that the techniques disclosed in the examples which follow represent techniques discovered by the inventors to function well in the practice of the invention, and thus can be considered to constitute particular modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Materials and Methods

Human samples. The phase I clinical trial was approved by the Food and Drug Administration and the University of Washington Human Subjects Division. All patients provided a written informed consent allowing immunological translational studies. Details about inclusion criteria of the trial were previously described (Disis et al., 2009).

Mouse model. All animal experiments were approved by the Vanderbilt Institutional Animal Care and Use Committee. Mice were housed in the accredited Animal Care Facility of the VUMC. FVB$^{MMTV/HER2}$ female transgenic mice expressing human HER2 cDNA under the control of the mouse mammary tumor virus (MMTV) promoter develop spontaneous mammary tumors with a latency of approximately 8 months (Finkle et al., 2004). These tumors were collected from the transgenic animals and then transplanted to the #1 mammary fat pad in wild-type FVB syngeneic female mice (4-6 weeks of age), allowed to grow to a volume of 200 mm$^3$ and treated with trastuzumab (Herceptin®) as previously described (Reyzer et al., 2004). Trastuzumab was administered in sterile isotonic saline at 30 mg/kg i.p. twice a week for four weeks. Control mice were treated with PBS. Tumor size was followed with calipers, and tumor volume was calculated by the formula (volume=width$^2$×length/2). Euthanasia was performed at 4 weeks post-treatment, unless otherwise stated. Blood samples were collected intermittently from orbital sinus with capillary tubes under general anesthesia or by heart puncture after euthanasia. FVB MMTV-polyoma virus middle T antigen (MMTV/PyMT) transgenic animals develop spontaneous mammary tumors and extensive pulmonary metastases under the control of MMTV promoter (Guy et al., 1992). These tumors do not express HER2. Sera from five FVB$^{MMTV/PyMT}$ mice with untreated human HER2-negative mammary tumors, from five normal untreated non-tumor bearing adult FVB$^{WT}$ mice, and from four FVB$^{MMTV/HER2}$ transgenic untreated mice were also examined and used as controls for experiments.

Antibodies. Trastuzumab (Heceptin®), bevacizumab (Avastin®), and rituximab (Rituxan®) from Genentech were purchased at the Vanderbilt University Hospital Pharmacy. Human IgG, human IgM, Human F(ab')$_2$ and human Fc used as controls were purchased from Jackson Immuno (West Grove, Pa.) or Sigma (St. Louis, Mo.). Mouse IgG2b was purchased from Bethyl (Montgomery, Tex.). Secondary peroxidase conjugated antibodies were obtained from Sigma-Aldrich.

Trastuzumab digestion. Trastuzumab F(ab')$_2$ was prepared by pepsin digestion. Pepsin was added to purified antibody in citrate buffer, pH 3.5 at a ratio of 5 µg of pepsin/mg of antibody. Antibodies were digested overnight at 37° C. PBS buffer was exchanged using a 30 kd cutoff Amicon Ultra-15 Centrifugal filter to remove digested antibody Fc fragments. F(ab')$_2$ preparations were analyzed by SDS-PAGE under reducing and non-reducing conditions and probed with HRP conjugated anti-Fc specific secondary antibodies on Western blots to determine F(ab')$_2$ integrity and absence of antibody Fc fragments.

Enzyme-Linked ImmunoSorbent Assay (ELISA). 384-well polystyrene microtiter plates (Nunc, Rochester, N.Y.) were coated overnight at 4° C. with trastuzumab or control antibodies at a concentration of 5 µg/mL PBS. Plates were blocked with PBS containing 0.1% Tween-20 (PBS-T) for 1 hr. Mouse serum samples were diluted in PBS-T and sequentially added to antibody-coated wells, in 3, 4 or 8 replicates. Samples were incubated for 2-3 hr at room temperature, and then washed with PBS-T. Peroxidase conjugated goat anti-mouse IgG (Fc-specific) and anti-human IgG (Fc-specific) were used to detect trastuzumab-bound mouse IgG or trastuzumab F(ab')$_2$-bound human IgG, respectively. After 1 hr incubation at room temperature plates were washed with PBS-T to remove unbound secondary antibody. Bound antibody was detected by adding hydrogen peroxide and ABTS (Pierce Chemical, Rockford, Ill.) to microtiter wells. After 30 min at room temperature, plates were read using a BiotekElx800nb plate reader operating at 405 nm. Results are representative of independent assays performed up to five times with reproducible results.

Generation of mouse hybridoma cell lines. Spleen of a selected mouse was collected at euthanasia and dissociated for B-cell combination with a myeloma cell line. Hybridoma cell fusion and subcloning by limiting dilution were performed according to previously published protocols, with minor modifications, using SP2/0-Ag14 myeloma cells as a fusion partner (Mernaugh and Mernaugh, 1995; Mernaugh et al., 1987). Clone cultures were allowed to grow and screened for their ability to bind trastuzumab immobilized in the plates. Wells of 384 well microtiter plates were coated with trastuzumab or control whole molecule antibody at a concentration of 10 µg/mL in PBS. Plates were washed and blocked for 30 min with PBS-T. Test hybridoma supernatant was added to each well and incubated for 1 hr at room temperature. Plates were washed with PBS-T after which HRP-conjugated goat anti-mouse IgG (Fc-specific) were added to each well. After 1 hr incubation at room temperature, plates were washed with PBS-T and ABTS containing hydrogen peroxide was added for color development. Plates were read as described previously. Results were considered positive when optical density readings were above two standard deviations plus average.

992-18 antibody-fine-specificity. In ELISA or dot blot, synthetic peptides were adsorbed directly onto microtiter plate wells or nitrocellulose membranes, respectively; then probed with 992-18 in solution. In immuno-mass spectrometry (IMS), protein A/G purified 992-18 monoclonal antibody was conjugated to NHS-Sepharose beads (G.E. Healthcare cat#17-0906-01) according to the manufacturer's instructions at a ratio of 1 mg of antibody per 1 ml of resin. Beads were blocked in PBS-T for 1 hr at room temperature. Two µg of each of peptide was dispensed to 72 separate 1.5 ml-centrifuge tubes with each tube containing 9.4 µl of beads in 50 µl of PBS-T. After 2.5 hr incubation at room temperature, the supernatant was aspirated off. The beads were washed with PBS-T and water to remove unbound peptide and salts, respectively. Water remaining on the beads was removed by aspiration. Beads were resuspended in 10-20 µl of MALDI-matrix ($\alpha$-cyano-4-hydroxycinnamic acid in acetonitrile) and incubated for 10-20 min at room temperature. After incubation, 2-5 µl of beads in MALDI-matrix were transferred from tubes and spotted onto a Bruker MTP 384 target stainless steel plate, then dried. Peptides bound to beads bearing the 992-18 antibody were detected using a Bruker Autoflex.

Cell lines. All cell lines were purchased from the American Type Culture Collection. Media and FBS were purchased from Invitrogen. The following growth media were used: for BT474, IMEM/10% FBS; for SKBR3, McCoy 5A/15% FBS; for SP2/0-Ag14 and hybridomas, RPMI/FBS/HAT, HT, L-glutamine and gentamicin. All cells were grown in a humidified 5% $CO_2$ humidified incubator at 37° C., except for the hybridomas, at 9% $CO_2$.

Cell based ELISA. Equal numbers of SKBR3 or BT474 cells were plated in 384 Well Optical Imaging Flat Clear Bottom Black Polystyrene TC-Treated Microplates® (Corning, Lowell, Mass.) and allowed to adhere and grow up to 90% confluence. Two hours prior to experiment, cells were washed and placed in medium without supplements. Medium was removed and cells were fixed in 10% acetone containing 3% hydrogen peroxide for 10 min. Cells were then blocked with PBS-T for 30 min at room temperature. Wells were exposed to therapeutic or mouse antibodies and incubated for 1-2 hr at room temperature. Plates were washed and anti-human IgG/HRP or anti-mouse IgG/HRP secondary antibody diluted 1/2000 in PBS-T was added to wells. Plates were washed again and ABTS containing hydrogen peroxide was added to each well for 10-30 min for color development. Plates were read using at 405 nm as described previously.

Immunofluorescence analysis (IFA). IFA was performed to identify the cellular localization of the cognate epitope of 992-18 MAb. BT474 and SKBR3 cells were cultured on glass cover-slips. Cells were fixed in 100% methanol, blocked in PBS-T/7% mouse serum and incubated with trastuzumab/Alexafluor$^{488}$ or 992-18/Alexafluor$^{647}$. Negative controls were bevacizumab/Alexafluor$^{488}$ and mIgG2b/Alexafluor$^{647}$. Independent cover slips were also incubated with combinations of two antibodies. Cells were then visualized using a Plan C-Apochromat-63×/1.4 oil differential interference contrast objective and Zeiss LSM 510 META NLO two-photon confocal laser-scanning microscope (Carl-Zeiss AG, Oberkochen, Germany).

Viability assay. For cell viability assay, cells were plated in 96-well or in 384-well plates at $1 \times 10^3$ cells/well or at $0.25 \times 10^3$ cells/well, respectively. After 24 hr, cells were exposed to increasing concentrations of 992-18 MAb, of its isotype control mIgG2b, or of trastuzumab (used as positive control). After 48 hr of antibody exposure, cell viability was determined by the Premixed WST-1 assay (Clontech, Mountain View, Calif.) according to manufacturer instructions. This colorimetric assay quantifies cell viability based on the enzymatic cleavage of the tetrazolium salt WST-1 to a water-soluble formazan dye by mitochondrial dehydrogenases from viable cells. The greater the number of metabolic active cells, the darker the formazan dye. Formazan dye was detected at 450 nm after 1 hr. The 655 nm reference filter was used to decrease background.

Statistical considerations. Statistical analysis of in vitro experiments and animal models was done using a two-tailed, nonparametric Mann-Whitney test for independent variables and Wilcoxon Signed-Rank test for dependent variables. Samples were tested in 2, 3, 4 or 8 replicates and experiments were repeated at least twice. Univariate Cox regression analysis of progression free survival in patients according to TFabR-antibodies optical density (OD) was performed. In this analysis TFabR-antibodies OD was log transformed and entered as a continuous variable. Spline of log TFabR-antibodies was used to evaluate if there was any non-linear association between TFabR-antibodies and the risk of disease progression. The non-linearity was insignificant. In order to save the degree of freedom, the model was reduced by using linear term of log TFabR-antibodies. Significance of the univariate Cox regression is expressed for the linear model. P values were considered significant if <0.05. SPSS version 16.0 and Microsoft Office Excel 2007 for Windows were used for analysis.

Example 2

Results

Figure 7:
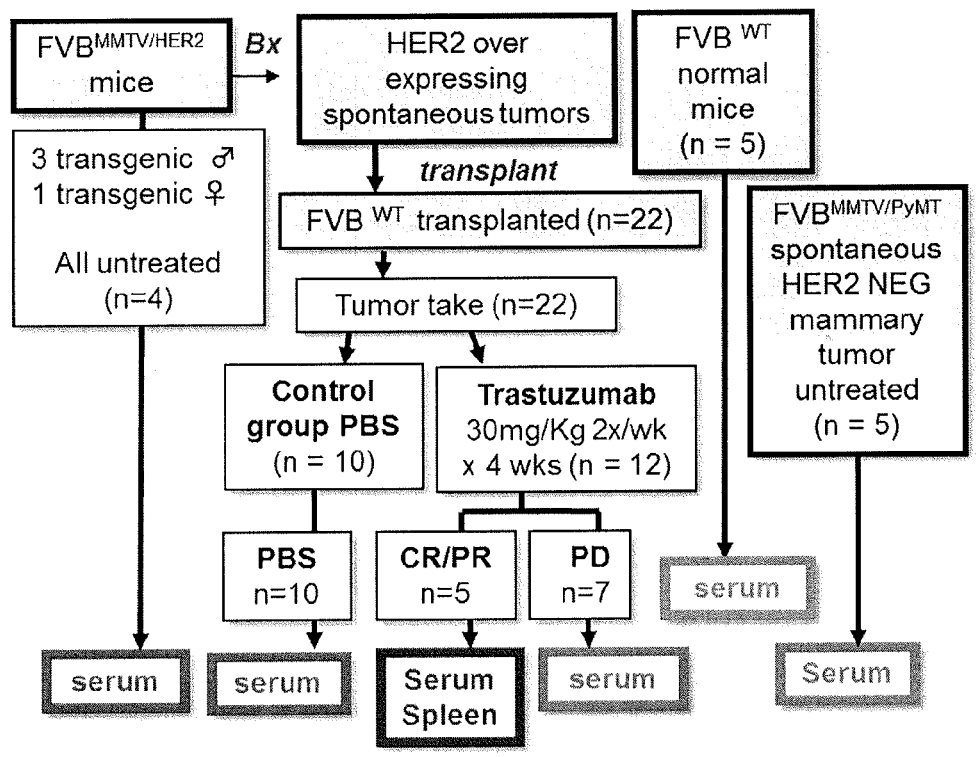
FIG. 7. Animal study design. First cohort of mice. WT, wild type; MMTV, Mouse mammary tumor virus; PyMT, Polyoma middle T antigen; HER2, Human Epidermal Receptor 2; FVB, mouse strain (Friend leukemia virus B); PBS, Phosphate buffered saline; CR, complete remission; PR, partial remission; PD, progressive disease.

MMTV/HER2 tumor responses to trastuzumab associate with presence of TR-antibodies in mouse sera. In order to study the humoral responses to trastuzumab and its potential association with treatment results, the inventors initially studied serum samples of mice from a well-established trastuzumab treatment mouse model (Finkle et al., 2004). Wild-type FVB mice were transplanted with syngeneic spontaneous huHER2-overexpressing mouse mammary tumors arising in $FVB^{MMTV/HER2}$ transgenic mice. Tumors were allowed to grow. Mice were subsequently treated with trastuzumab or PBS. All tumors from PBS treatment group progressed in size over time. In the trastuzumab group, five mice responded and seven mice had disease progression. FIG. 7 shows details about this mouse cohort.

TR-antibodies in mouse sera were detected by ELISA. In tumor-bearing mice, tumor response to treatment was directly related to detectable TR-antibodies in mouse sera (FIG. 1A). Every responder mouse had increased absorbance of TR-antibodies in serum. Mice that were treated with PBS only or with trastuzumab, but had progressive disease (PD), had lower absorbance of TR-antibodies ('Responders' vs. 'PD', or 'Responders' vs. 'PBS', p=0.014 and p=0.002 respectively; Mann-Whitney two-tailed). Comparisons between responders and all other groups were statistically significant. Absorbance values for TR-antibodies in the other control groups were even lower than what was detected for PD group, or undetectable.

Figure 1B:
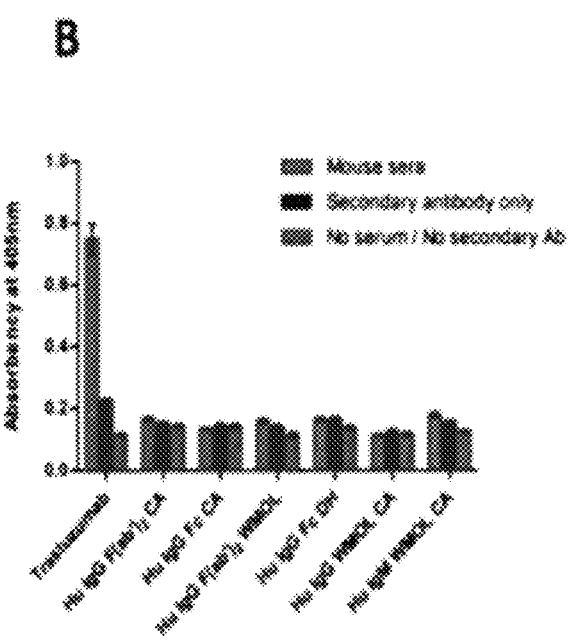

In order to rule out nonspecific reactivity from the mice to human components of trastuzumab molecule as source for the unexpected results, mouse sera were also tested against commercially available human IgG, human IgM, human Fab and human Fc fragments, but no significant antibody binding activity was detected against any of these controls (FIG. 1B). These findings suggest the existence of a specific humoral response in mice treated with trastuzumab, which targets epitopes from the therapeutic antibody and is associated with tumor response to therapy in mice.

Figure 1C:
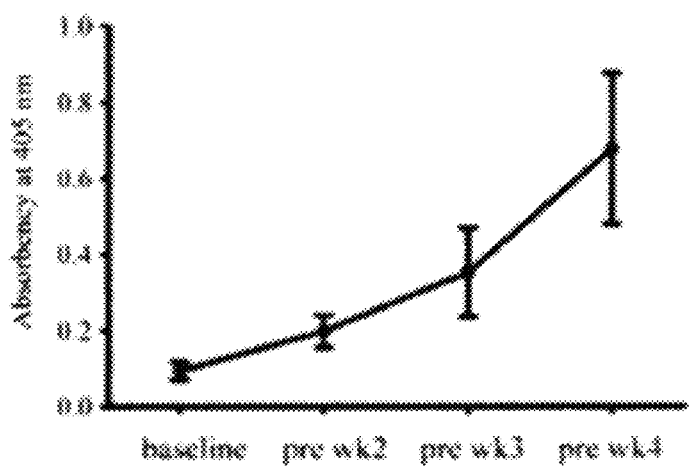
Figure 1D:
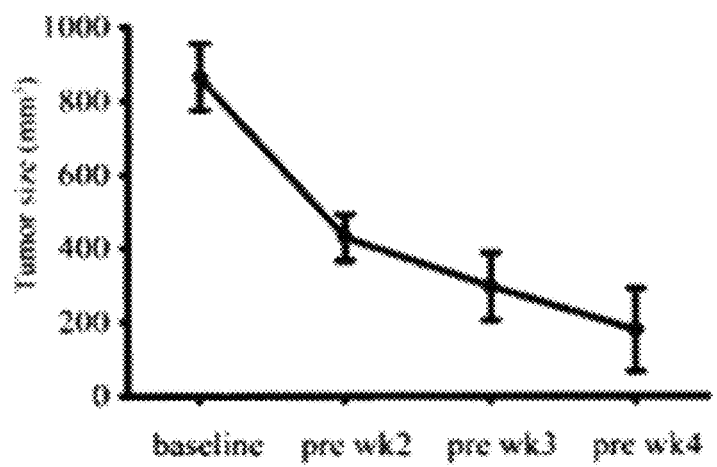

To evaluate the kinetics of TR-antibodies response in mice, and to expand the sample and power for the initial counterintuitive results, a new cohort of sixteen $FVB^{WT}$ mice transplanted with HER2 overexpressing mammary tumors and treated with the same schedule of trastuzumab was evaluated. Blood samples were collected under anesthesia at baseline and then weekly, before next trastuzumab administration. There was a consistent increase in the average of absorbance of TR-antibodies at 1:40 serum dilution as tumors shrunk on trastuzumab treatment overtime (FIGS. 1C-D).

Taken together, the results from two independent mouse cohorts suggest that, in $FVB^{WT}$ mice bearing HuHER2 overexpressing tumors, exposure to trastuzumab produces a humoral response characterized by the production of antibodies that are reactive with trastuzumab. Detection of these antibodies by ELISA two to three weeks after initial exposure is associated with tumor shrinkage. In addition, the abundant human derived components present in the trastuzumab framework did not represent per se an obstacle for tumor response, even after seroconversion upon exposure to trastuzumab. Data presented did not support the hypothesis that these anti-MAb could be blocking antibodies. The inventors' new hypothesis was that the presence of detectable TR-antibodies could be a marker of response to trastuzumab therapy. However, the above mentioned findings could be restricted to the utilized mouse model, and potentially lacking clinical relevance.

In patients with breast cancer treated with trastuzumab, the presence of trastuzumab F(ab')$_2$-reactive antibodies in serum was associated with lower risk of progressive disease. If the preclinical results were clinically relevant, they would predict that patients with detectable TR-antibodies would have better clinical response or longer progression free survival when treated with trastuzumab. To detect TR-antibodies in human serum by ELISA, plates were coated with purified trastuzumab F(ab')$_2$ fragments instead of with trastuzumab whole molecule.

Figure 2:
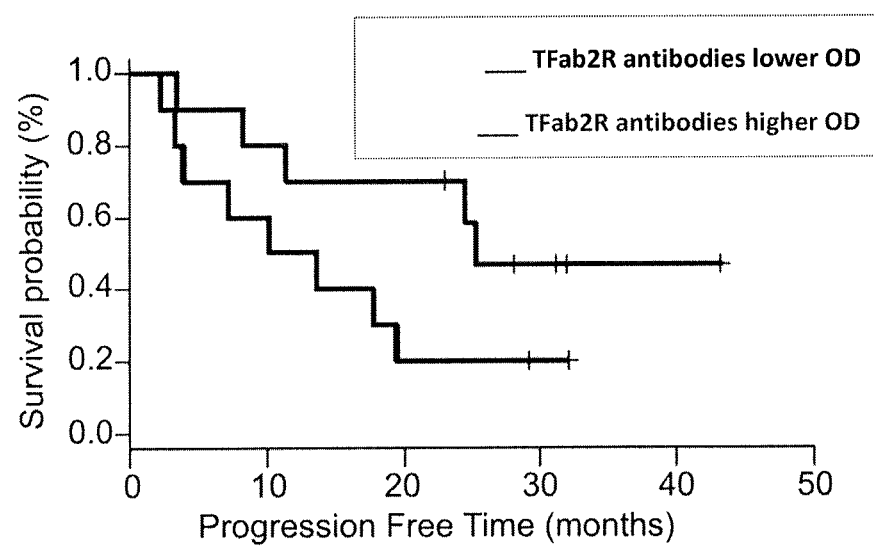
FIG. 2. In patients the presence of TFabR-antibodies was associated with lower probability of progressive disease. Retrospective and blinded analysis of baseline samples from a phase I vaccine trial (Disis et al., 2009) for the presence of TFabR-antibodies by ELISA. Lower absorbency is detected among patients who developed progressive disease during the clinical follow up period. Antibodies directed to Trastuzumab Fc epitopes were not evaluated in these experiments. Abbreviations: OD, optical density; TFabR-antibodies, Trastuzumab F(ab')$_2$-reactive antibodies.
Figure 8:
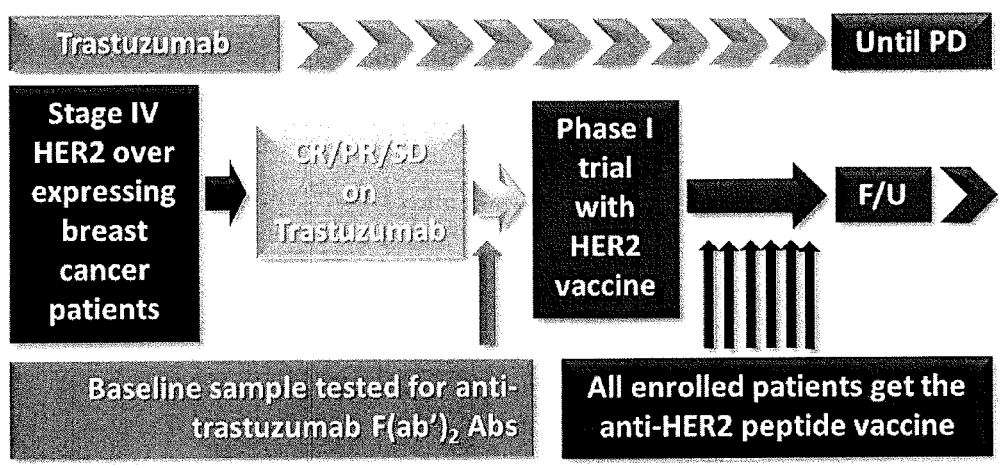
FIG. 8. Phase I clinical trial design (Disis et al., 2009). HER2, Human Epidermal Receptor 2; F/U, follow up; CR, complete remission; PR, partial remission; PD, progressive disease.

Patients with stage IV HER2-overexpressing breast cancer achieving disease stabilization or clinical response while treated with trastuzumab were enrolled in a phase I vaccine trial (Disis et al., 2009). FIG. 8 presents the design of this trial. With a median of 36 months, fourteen patients developed progressive disease. Serum samples were collected prior to vaccination. The analysis of these samples for trastuzumab F(ab')$_2$-reactive antibodies (TFabR-antibodies) was retrospective and blinded. Univariate Cox regression analysis revealed that higher absorbance of TFabR-antibodies in ELISA was significantly associated with lower risk of progressive disease in this small sample (Univariate Cox regression analysis; p=0.023) (FIG. 2).

This finding confirmed the clinical relevance of TR-antibodies detection. These naturally-occurring antibodies could represent a marker of response to therapy and/or of better immunity. Moreover, they could carry intrinsic pharmacologic properties supportive of trastuzumab anti-tumoral effects. Next would be to characterize these antibodies, including defining their fine specificity and evaluating potential anti-tumor properties. Using serum to evaluate fine-specificity of humoral responses to large proteins was technically problematic due to its polyclonal nature. Therefore, the inventors produced hybridomas from spleen B-cells of responder mice and generated anti-trastuzumab MAbs.

Figure 3:
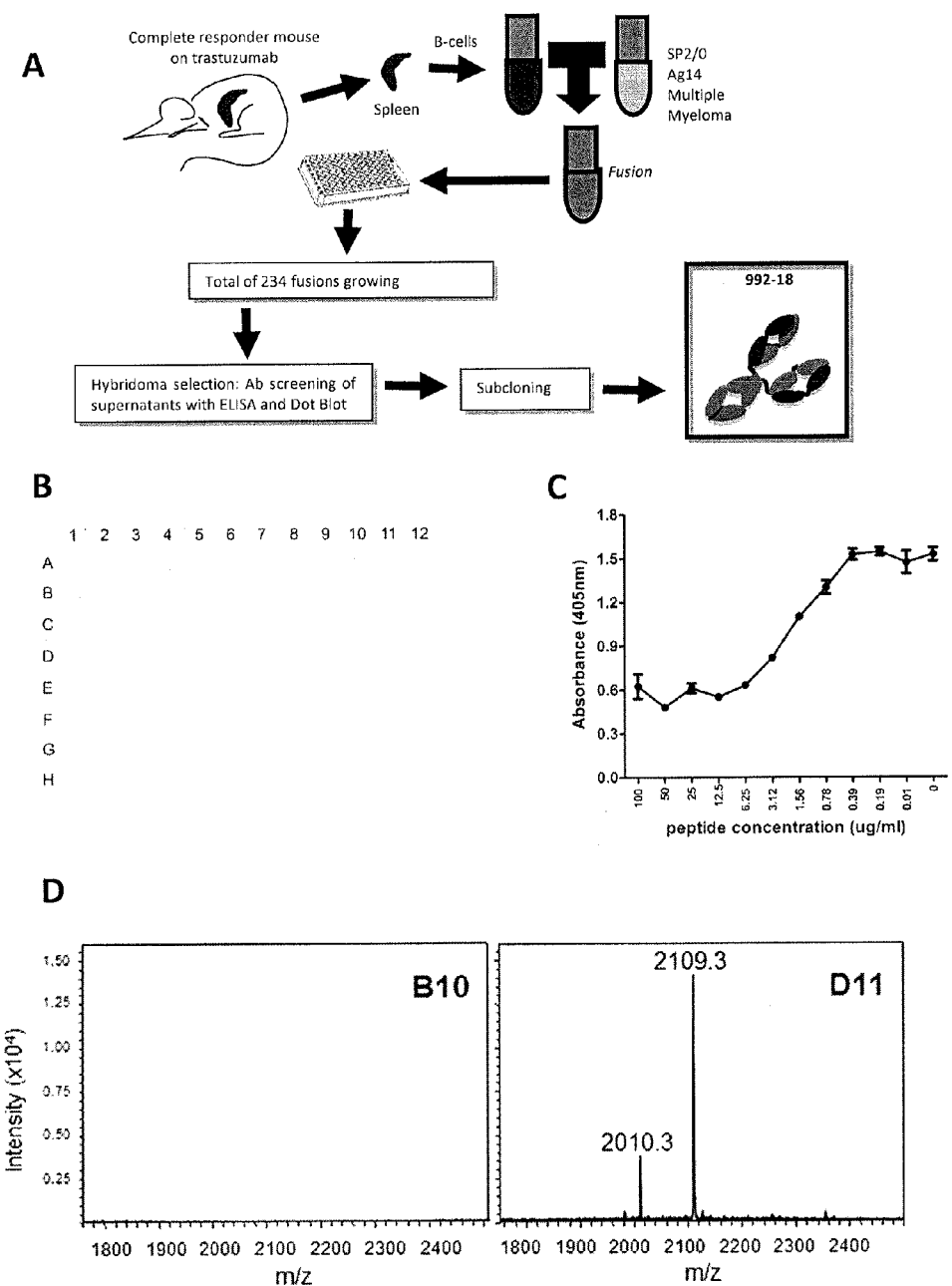
FIGS. 3A-D. B-cell clones from mouse spleen produce anti-trastuzumab specific antibodies.

Fine specificity: B cell clones from mouse spleen produce anti-trastuzumab specific antibodies. To allow the study of the binding sites of TR-antibodies on trastuzumab, hybridomas were generated using SP2/0-Ag14 myeloma cell line and spleen B-cells from one of the responder mice. That mouse had detectable circulating TR-antibodies at the end of trastuzumab treatment. Clones were selected by producing specific anti-trastuzumab antibodies. Several mouse anti-trastuzumab monoclonal antibodies (MAbs) were produced. One of these was a MAb designated 992-18 (FIG. 3A).

Dot blot, ELISA and ImmunoMass Spectrometry (IMS) assays were used to determine 992-18 antibody fine-specificity. The 992-18 MAb binds to denatured trastuzumab in Western blots (data not shown), suggesting that 992-18 recognizes a linear epitope on trastuzumab. For dot blot and ELISA, 992-18 was assayed against 72 overlapping trastuzumab synthetic peptides representing trastuzumab antibody heavy and light chain domains as antigens. The 992-18 MAb bound to a trastuzumab peptide placed in the position D11 of the plates and nitrocellulose membrane. In the competition ELISA, trastuzumab was immobilized on a plate and wells exposed to a constant concentration of 992-18 and decreasing concentration of D11 synthetic peptide. Higher concentrations of D11 peptide inhibited the binding of 992-18 to trastuzumab. Secondary antibody alone did not bind to D11 peptide (data not shown).

In IMS, 992-18 was immobilized onto beads and used to capture peptides out of solution. Six pairs of overlapping peptides bound to 992-18 on beads. These included the overlapping peptides designated D10 (SFFLYSKLT VDKSRWQQG (SEQ ID NO:3)) and D11 (VDKSRWQQGNVFSCSVMH (SEQ ID NO:2)). Of the 72 peptides analyzed, only D11 interacted with 992-18 in IMS, ELISA and dot blot assays. It was concluded that the trastuzumab epitope recognized by 992-18 is VDKSRWQQG (SEQ ID NO:1). This site is located at the trastuzumab Fc heavy chain, near the C-terminus. These experiments also confirmed that B-cells collected from the spleen of a responder mouse produced anti-trastuzumab antibodies. If this phenomenon is also occurring in humans treated with trastuzumab, the inventors would predict that antibodies from patients' sera would also bind to trastuzumab synthetic peptides, potentially including the D11 peptide.

Figure 4:
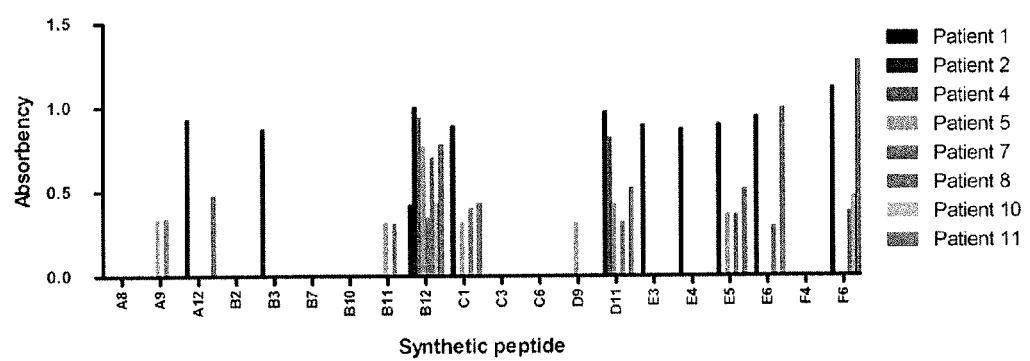
FIG. 4. Patient's sera react against several trastuzumab synthetic peptides, including the peptide targeted by the MAb 992-18. Breast cancer patients on ongoing trastuzumab treatment and presenting clinical benefit were enrolled in a HER2 vaccine trial (Disis et al., 2009). Serum was collected prior to vaccination and assayed against trastuzumab peptides immobilized on a plate. Patient's serum reacted against D11 as well as against several other synthetic peptides located in the constant and variable domains. Results of a representative experiment in which absorbance corresponds to average of 8 replicate wells per sample. Peptides selected for statistical significance had absorbance two standard deviations above average.

Patient's sera react against several trastuzumab synthetic peptides, including D11. After defining the cognate epitope of 992-18 on trastuzumab, with the aim of studying the fine-specificity of human TR-antibodies, serum samples from patients accrued to the previously mentioned phase I trial (Disis et al., 2009) were screened against the 72 overlapping trastuzumab synthetic peptides (FIG. 4). Patient's serum reacted against several peptides corresponding to trastuzumab's constant and variable domains, as well as heavy and light chains, including against D11 itself. Results indicate that patients produce a polyclonal response to trastuzumab epitopes, with some antibodies resembling the mouse MAb 992-18 in their specificity and targeting the synthetic peptide D11. This result validates the use of 992-18 in forthcoming experiments.

After confirming that TFabR-antibodies could potentially represent predictor biomarkers of trastuzumab treatment response and defining some aspects of their fine specificity, the inventors addressed the question of additional potential anti-tumoral properties of these naturally occurring antibodies. For this, 992-18 was used as a model. They hypothesize that, if 992-18 had any direct effect on tumor cells, the inventors should demonstrate it binding to cells, at least with trastuzumab.

The 992-18 MAb binds directly to SKBR3 and BT474 cells independently of trastuzumab. FIG. 5A presents results of trastuzumab and other therapeutic antibodies used as controls binding to the HER2-overexpressing SKBR3 cells, in the presence or absence of 992-18. The absorbance of trastuzumab binding to SKBR3 cells was elevated and similar when cells were concomitantly exposed to 992-18 or to its isotype control, mouse IgG2b (FIG. 5A). This suggests that the 992-18 MAb does not change significantly trastuzumab binding to SKBR3 cells. FIG. 5B shows binding of 992-18 to cells in the presence or absence of trastuzumab or other therapeutic antibodies. The 992-18 MAb significantly bound to SKBR3 cells directly (992-18 vs. mIgG2b; p=0.002).

To locate the cognate epitope of 992-18 on cells, the inventors performed immunofluorescence analysis (IFA) using 992-18, its isotype mIgG2b, trastuzumab and bevacizumab. FIGS. 5C-D show 992-18 (red) binding to an antigen most likely located in the cytoplasm of the cell lines. Trastuzumab (green) bound to HER2 at the membrane. There was no significant binding of mIgG2b or bevacizumab to cell lines (not shown).

FIGS. 6A-B shows results of viability assays in which breast cancer cell lines were treated with 992-18 or control antibodies. Cells exposed to 992-18 were significantly less viable than those treated with its isotype control mIgG2b. Trastuzumab was used as a positive control. Taking together these findings, they indicate that the anti-trastuzumab MAb 992-18 may function as a heteroclitic antibody (Gjelstrup et al., 2011; Baert et al., 2003), binding also to an intracellular component of SKBR3 and BT474 cells, regardless of the presence of trastuzumab, and possibly having pharmacologic anti-proliferative/pro-apoptotic effects in vitro. The epitope on SKBR3 or BT474 cells that is targeted by 992-18 has not been defined yet.

Example 3

Discussion

Based on experience with the use of mouse antibodies to treat cancer patients, antibody immunogenicity with the production of human anti-mouse blocking antibodies has been generally thought to be detrimental to the anti-tumoral effect of therapeutic MAbs used in Oncology (Oldham and Dillman, 2008). Recombinant methodologies have allowed the production of therapeutic MAbs with higher percentages of human content to decrease antibody immunogenicity, reduce hypersensitivity reactions and decrease the anti-antibody response. In autoimmune diseases, the anti-MAbs produced by patients in response to anti-TNF treatment have been characterized and implicated with treatment failure (Baert et al., 2003; Bartelds et al., 2007). In HER2-overexpressing malignancies, the human anti-monoclonal response has not been evaluated in deep until now. This is the first detailed description of the presence of anti-trastuzumab antibodies in the serum of patients treated with trastuzumab for breast cancer.

Here, in a transgenic mouse model using immunocompetent mice, prospective serum collection and hybridoma generation studies support the hypothesis that animals specifically reacted to epitopes present in trastuzumab. Surprisingly, the detection of anti-trastuzumab antibodies in treated mice was associated with response to therapy with trastuzumab. This result was confirmed in two independent mouse cohorts and did not support the previous concept that all arising anti-therapeutic antibodies are blocking antibodies.

Subsequent experiments with human samples confirmed the clinical significance of the above mentioned findings. Patients with metastatic HER2-overexpressing breast cancer treated with trastuzumab and selected by achieving clinical benefit from this therapy were enrolled in a phase I clinical trial (Disis et al., 2009). Baseline samples from this trial were retrospectively tested. In that population, higher optical density of TFabR-reactive antibodies was associated with longer progression free survival probability. Many patients had pre-existing immunity specific for HER2 and other breast cancer antigens. After enrollment to the trial all patients received the HER2 vaccine and continued trastuzumab therapy. HER2 epitope spreading was elicited with vaccination. It is unclear if this phenomenon also extended to trastuzumab epitopes, or if trastuzumab as an antigen can induce epitope spreading that elicits effective immune responses in patients who benefit from its use.

To further study the TR-antibodies produced in response to trastuzumab therapy and associated with better disease outcome, anti-trastuzumab MAb were produced using B-cells from the spleen of mice that responded to trastuzumab therapy. One of these was a MAb designated 992-18. The 992-18 MAb was assayed against 72 overlapping trastuzumab synthetic peptides by dot blot, direct and competitive ELISA and by mass spectrometry to determine its fine-specificity. The trastuzumab epitope recognized by 992-18 is VDKSRWQQG (SEQ ID NO:1). This peptide sequence is located near the trastuzumab Fc heavy chain C-terminus. Therefore, 992-18 is not a trastuzumab anti-idiotype antibody. However, the concurrent presence of a fully developed idiotypic cascade involving HER2 and trastuzumab in responders as a cause for production of anti-trastuzumab antibodies and better outcome could not be excluded.

Human serum was also screened against the synthetic trastuzumab peptides. Patients had detectable antibodies directed to peptides from different domains of trastuzumab molecule (constant and variable regions; light and heavy chains). Most of the patients who had detectable anti-trastuzumab humoral response reacted also with the cognate epitope of 992-18 on trastuzumab (D11 peptide). This finding validated the subsequent use of 992-18 in mechanistic pre-clinical experiments. A limitation of this approach was that fine specificity of response to trastuzumab conformational epitopes as well as cellular responses to the therapeutic antibody were not evaluated. Moreover, in this study it was not possible to determine if anti-trastuzumab antibodies were present in patients' serum prior to trastuzumab exposure.

Anti-trastuzumab antibodies produced in response to therapy could simply represent surrogate markers of benefit from therapy or of better immunity. If this is the case, these antibodies could be tested as predictors of benefit of trastuzumab in larger patient populations, and potentially in the adjuvant setting, when breast tumor measurements are no longer a possibility and patients undergo a yearlong chemotherapy/trastuzumab-based therapy. Prospective studies sized to assure appropriate power would be needed to address if anti-trastuzumab antibodies are clinically useful as predictive biomarkers, as well as to establish assay accuracy and meaningful cut-offs.

Apart from their potential as biomarkers, anti-trastuzumab antibodies may also have anti-tumor effects of their own, or work increasing trastuzumab activity. The 992-18 MAb effects on viability of two breast cancer cell lines were presented here. Other hypothetical pharmacologic effects of this and of other non-blocking anti-trastuzumab antibodies that were not evaluated here could include improving trastuzumab pharmacokinetics, enhancing trastuzumab/HER2 binding, stability or internalization (Ben-Kasus et al., 2009), as well as increasing antibody dependent cellular cytotoxicity, consequently improving overall trastuzumab anti-tumor effects. Taking all this together, the inventors conclude that a degree of immunogenicity against the therapeutic antibody could be important for its therapeutic action in oncology. This concept is especially relevant for the development of new anti-tumoral antibodies and of biosimilars, as well as in vaccine development.

In summary, results of this study represent the first report of the presence of anti-trastuzumab antibodies in patients and of their potential as biomarkers of benefit from therapy. Exposure to trastuzumab elicits humoral responses against epitopes present in different segments of the therapeutic antibody, and the presence of detectable TR-antibodies in serum of patients is associated with better outcome to trastuzumab therapy. Results also suggest that the resultant humoral response to trastuzumab in cancer subjects is potentially capable of producing antibodies that directly target cancer cells.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

XI. References

The following references and any others listed herein, to the extent that they provide exemplary procedural or other details supplementary to those set forth herein, are specifically incorporated herein by reference in their entirety.

U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,366,241
U.S. Pat. No. 4,472,509
U.S. Pat. No. 4,938,948
U.S. Pat. No. 5,021,236
U.S. Pat. No. 5,196,066
U.S. Pat. No. 5,399,363
U.S. Pat. No. 5,466,468
U.S. Pat. No. 5,543,158
U.S. Pat. No. 5,641,515
U.S. Pat. No. 6,150,584
U.S. Pat. No. 6,800,738
Abbondanzo et al., *Breast Cancer Res. Treat.*, 16:182(151), 1990.
Allred et al., *Arch. Surg.*, 125(1):107-113, 1990.
Antibodies: A Laboratory Manual, Cold Spring Harbor Laboratory, 1988.
Atherton et al., *Biol. of Reproduction*, 32:155-171, 1985.
Baert et al., *NE J. Med.*, 348:601, 2003.
Bartelds et al., *Annals Rheumatic Dis.*, 66:921, 2007.
Bei et al., *Oncogene*, 18(6):1267-1275, 1999.
Ben-Kasus et al., *Proc. Natl. Acad. Sci.*, 106:3294, 2009.
Berberian et al., *Science*, 261:1588-1591, 1993.
Bird et al., *Science*, 242:423-426, 1988.
Bowie et al., *Science*, 253(5016):164-170, 1991
Brown et al. *Immunol. Ser.*, 53:69-82, 1990.
Cleary et al., *Trends Microbiol.*, 4:131-136, 1994.
De Jager et al., *Semin. Nucl. Med.*, 23(2):165-179, 1993.
Dholakia et al., *J. Biol. Chem.*, 264:20638-20642, 1989.
Disis et al., *Cancer Res.*, 54(1):16-20, 1994.
Disis et al., *J. Clin. Oncol.*, 15(11):3363-3367, 1997.
Disis et al., *J. Clin. Oncol.*, 27:4685, 2009.

Doolittle and Ben-Zeev, Methods Mol. Biol., 109:215-237, 1999.
Finkle et al., Clin. Cancer Res., 10:2499, 2004.
Gjelstrup et al., Molecul. Immunol., 2011 (ahead of print].
Goding, In: Monoclonal Antibodies: Principles and Practice, 2d ed., Academic Press, Orlando, Flor., pp 60-61, 65-66, 1986.
Gulbis and Galand, Hum. Pathol., 24(12):1271-1285, 1993.
Guy et al., Mol. Cell. Biol., 12:954, 1992.
Harlow and Lane, In: Antibodies: A Laboratory Manual, Cold Spring Harbor Laboratory, Cold Spring Harbor, N.Y., 346-348, 1988.
Jakobovits et al., Nature, 362:255-258, 1993.
Jakobovits et al., Proc. Natl. Acad. Sci. USA, 90:2551, 1993.
Jones et al., Nature, 321:522-525, 1986.
Kang et al., Science, 240:1034-1036, 1988.
Khatoon et al., Ann. of Neurology, 26:210-219, 1989.
King et al., J. Biol. Chem., 269:10210-10218, 1989.
Kohler et al., Methods Enzymol, 178:3-35, 1989.
Kozbor, J. Immunol., 133(6):3001-3005, 1984.
Kreier et al., In: Infection, Resistance and Immunity, Harper & Row, NY, 1991.
Lenert et al., Science, 248:1639-1643, 1990.
McCafferty et al., Nature, 348:552-553, 1990.
Mernaugh and Mernaugh, In: Molecular Methods in Plant Pathology, Singh and Singh (Eds.), CRC Press, FL, 343-358, 1995.
Mernaugh et al., Biotechnol. Tech., 1:31, 1987.
Nakamura et al., In: Handbook of Experimental Immunology (4$^{th}$ Ed.), Weir et al., (eds). 1:27, Blackwell Scientific Publ., Oxford, 1987.
Oldham and Dillman, J. Clin. Oncol., 26:1774, 2008.
O'Shannessy et al., J. Immun. Meth., 99:153-161, 1987.
Owens & Haley, J. Biol. Chem., 259:14843-14848, 1987.
Potter & Haley, Meth. Enzymol., 91:613-633, 1983.
Remington's Pharmaceutical Sciences" 15th Edition, pages 1035-1038 and 1570-1580, 1990.
Remington's Pharmaceutical Sciences, 18th Ed. Mack Printing Company, 1289-1329, 1990.
Reyzer et al., Cancer Res., 64:9093, 2004.
Riechmann et al., Nature, 332(6162):323-327, 1988.
Sasso et al., J. Immunol., 142:2778-2783, 1989.
Shorki et al., J. Immunol., 146:936-940, 1991.
Silvermann et al., J. Clin. Invest., 96:417-426, 1995.
Verhoeyen et al., Science, 239:1534-1536, 1988.

What is claimed is:

1. An isolated monoclonal antibody that reacts immunologically with an epitope characterized by the primary sequence VDKSRWQQG (SEQ ID NO: 1).

2. The isolated monoclonal antibody of claim 1, wherein said antibody reacts immunologically with an epitope characterized by the primary sequence VDKSRWQQGNVFSCSVMH (SEQ ID NO:2) and/or SFFLYSKLTVDKSRWQQG (SEQ ID NO:3).

3. The isolated monoclonal antibody of claim 1, wherein said monoclonal antibody is an IgG antibody.

4. The isolated monoclonal antibody of claim 1, wherein said monoclonal antibody hinds to a HER2-positive breast cancer cell.

5. The isolated monoclonal antibody of claim 1, wherein said monoclonal antibody is a recombinant single-chain variable antibody fragment, a Fv fragment, a Fab antibody fragment or is humanized.

6. A hybridoma that produces a monoclonal antibody that reacts immunologically with an epitope characterized by the primary sequence VDKSRWQQG (SEQ ID NO: 1).

7. The hybridoma claim 6, wherein said monoclonal antibody reacts immunologically with an epitope characterized by the primary sequence VDKCSRWQQGNVFSCSVMH (SEQ ID NO:2) and/or SEFLYSKLTVDKSRWQQG (SEQ ID NO:3).

8. The hybridoma of claim 6, wherein said monoclonal antibody is an IgG antibody.

9. The hybridoma of claim 6, wherein said monoclonal antibody binds to a HER2-positive breast cancer cell.

10. The hybridoma of claim 6, wherein said monoclonal antibody is a recombinant single-chain variable antibody fragment, a Fv fragment, or a humanized antibody.

11. A composition comprising an isolated monoclonal antibody that reacts immunologically with an epitope characterized by the primary sequence VDKSRWQQG (SEQ ID NO: 1) in a pharmaceutically acceptable buffer, carrier or diluent.

12. The composition of claim 11, wherein said isolated monoclonal antibody reacts immunologically with an epitope characterized by the primary sequence VDKSRWQQGNVFSCSVMH (SEQ ID NO:2) and/or SFFLYSKLTVDKSRWQQG (SEQ ID NO:3).

13. The composition of claim 11, wherein said isolated monoclonal antibody is an IgG antibody.

14. The composition of claim 11, wherein said monoclonal antibody binds to a HER2-positive breast cancer cell.

15. The composition of claim 11, wherein said isolated monoclonal antibody is a recombinant single-chain variable antibody fragment, a Fv fragment, a Fab antibody fragment or is humanized.

* * * * *

UNITED STATES PATENT AND TRADEMARK OFFICE
CERTIFICATE OF CORRECTION

PATENT NO. : 8,486,413 B2  Page 1 of 1
APPLICATION NO. : 13/314841
DATED : July 16, 2013
INVENTOR(S) : Paula R. Pohlmann et al.

It is certified that error appears in the above-identified patent and that said Letters Patent is hereby corrected as shown below:

In the Claims:

In claim 4, column 37, line 13, delete "hinds" and insert --binds-- therefor.

In claim 7, column 37, line 24, delete "VDKCSRWQQGNVFSCSVMH" and insert --VDKSRWQQGNVFSCSVMH-- therefor.

In claim 7, column 37, line 25, delete "SEFLYSKLTVDKSRWQQG" and insert --SFFLYSKLTVDKSRWQQG-- therefor.

Signed and Sealed this
Thirteenth Day of May, 2014

Michelle K. Lee
*Deputy Director of the United States Patent and Trademark Office*